United States Patent
Kalorin et al.

(10) Patent No.: US 11,819,644 B2
(45) Date of Patent: Nov. 21, 2023

(54) METHOD AND APPARATUS FOR TREATING GENITOURINARY PROBLEMS

(71) Applicant: CJMI, LLC, Raleigh, NC (US)

(72) Inventors: Carmin Kalorin, Raleigh, NC (US); Jack Slovick, Nevis, MN (US); Michael Weddington, Wake Forest, NC (US); Ian Udell, Raleigh, NC (US); Laura Helton, Raleigh, NC (US)

(73) Assignee: CJMI, LLC, Raleigh, NC (US)

( * ) Notice: Subject to any disclaimer, the term of this patent is extended or adjusted under 35 U.S.C. 154(b) by 546 days.

(21) Appl. No.: 17/069,158

(22) Filed: Oct. 13, 2020

(65) Prior Publication Data

US 2021/0113819 A1    Apr. 22, 2021

Related U.S. Application Data

(60) Provisional application No. 62/965,721, filed on Jan. 24, 2020, provisional application No. 62/916,191, filed on Oct. 16, 2019.

(51) Int. Cl.
    *A61M 25/10*      (2013.01)
    *A61M 25/00*      (2006.01)
    (Continued)

(52) U.S. Cl.
    CPC ........... *A61M 25/10* (2013.01); *A61L 29/085* (2013.01); *A61L 29/16* (2013.01);
    (Continued)

(58) Field of Classification Search
    CPC .............. A61M 25/10; A61M 25/1011; A61M 25/007; A61M 25/0032; A61M 25/0023;
    (Continued)

(56) References Cited

U.S. PATENT DOCUMENTS

| | | |
|---|---|---|
| X583382 | 5/1897 | Luer |
| 3,394,705 A * | 7/1968 | Abramson ........ A61M 25/0017 604/104 |

(Continued)

FOREIGN PATENT DOCUMENTS

| | | |
|---|---|---|
| EP | 1210052 B1 | 1/2008 |
| EP | 3060136 A1 | 8/2016 |

(Continued)

OTHER PUBLICATIONS

Lieberman, Robert P., Cummings, Kenneth B., Leslie, Stephen W.; Sheathed catheter system for fluoroscopically guided retrograde catheterization, and brush and forceps biopsy of the upper urinary tract; The Journal of Urology; Mar. 1984; vol. 131(3); pp. 450-453; doi: 10.1016/s0022-5347(17)50444-9; PMID: 6699983.

(Continued)

*Primary Examiner* — Tasnim Mehjabin Ahmed
(74) *Attorney, Agent, or Firm* — Gallium Law; Wesley Schwie, Esq.; Michael Bakke

(57) ABSTRACT

Apparatus and methods for treatment of bleeding and/or microbial infection of the genitourinary tract including a catheter and an insertable and removable medicament-delivery sheath for introducing a hemostatic and/or anti-microbial substance or the like. Some embodiments further include a light-delivery sheath and/or light-delivery-and-imaging sheath having a light-propagation channel, and a source of anti-microbial and/or imaging light in one or more wavelength bands, for example UVC light and/or light in the visible violet, blue or green wavelength ranges. Some embodiments include a display for captured images, and/or a motorized sheath-movement device configured to move one or more light-output ports. Some embodiments further include a light-propagation channel built into the catheter itself (such as one or more optical fibers) for the administration of anti-microbial ultraviolet light (and/or other wave- (Continued)

lengths of light) light along the catheter and/or at the distal end of the catheter to treat and/or prevent microbial (bacterial and/or fungal) infections.

21 Claims, 18 Drawing Sheets

(51) Int. Cl.
    *A61L 29/08*     (2006.01)
    *A61L 29/16*     (2006.01)
    *A61L 2/00*     (2006.01)

(52) U.S. Cl.
    CPC .... *A61M 25/0017* (2013.01); *A61M 25/0021* (2013.01); *A61L 2/0047* (2013.01); *A61L 2202/14* (2013.01); *A61L 2400/04* (2013.01); *A61M 25/007* (2013.01); *A61M 25/0023* (2013.01); *A61M 25/0032* (2013.01); *A61M 25/1011* (2013.01); *A61M 2025/0056* (2013.01); *A61M 2025/0057* (2013.01); *A61M 2025/1043* (2013.01); *A61M 2205/0205* (2013.01); *A61M 2205/05* (2013.01); *A61M 2205/583* (2013.01); *A61M 2205/587* (2013.01); *A61M 2210/1085* (2013.01)

(58) Field of Classification Search
    CPC .......... A61M 25/0021; A61M 25/0017; A61M 2025/1043; A61M 2025/0057; A61M 2025/0056; A61M 2205/0205; A61M 2205/05; A61M 2205/583; A61M 2205/587; A61M 2210/1085
    See application file for complete search history.

(56) References Cited

U.S. PATENT DOCUMENTS

| | | | |
|---|---|---|---|
| 5,702,373 A * | 12/1997 | Samson | A61M 25/005 604/526 |
| 6,165,127 A | 12/2000 | Crowley | |
| 6,527,737 B2 | 3/2003 | Kaneshige | |
| 6,898,454 B2 | 5/2005 | Atalar et al. | |
| 7,613,478 B2 | 11/2009 | Jabri et al. | |
| 8,409,172 B2 | 4/2013 | Moll et al. | |
| 8,784,461 B2 | 7/2014 | Webb et al. | |
| 9,125,573 B2 | 9/2015 | Koyrakh et al. | |
| 9,474,811 B2 | 10/2016 | Sharma | |
| 9,550,005 B2 | 1/2017 | Lin et al. | |
| 10,022,183 B2 | 7/2018 | Brucker et al. | |
| 10,304,188 B1 | 5/2019 | Kumar | |
| 10,315,023 B2 | 6/2019 | Mantri et al. | |
| 10,335,322 B2 | 7/2019 | Doshi et al. | |
| 2005/0245840 A1 | 11/2005 | Christopherson et al. | |
| 2008/0119785 A1 | 5/2008 | Ramsey et al. | |
| 2010/0137721 A1 | 6/2010 | Rose et al. | |
| 2014/0163467 A1 | 6/2014 | Ramsey et al. | |
| 2015/0231287 A1 * | 8/2015 | Lin | A61M 25/0097 607/80 |
| 2016/0199230 A1 | 7/2016 | Doshi et al. | |
| 2016/0256665 A1 | 9/2016 | Doshi et al. | |
| 2018/0264247 A1 | 9/2018 | Mantri et al. | |
| 2019/0076572 A1 | 3/2019 | Saber | |
| 2019/0231359 A1 | 8/2019 | Mantri et al. | |
| 2019/0232036 A1 | 8/2019 | Mantri et al. | |
| 2019/0232037 A1 | 8/2019 | Mantri et al. | |
| 2019/0328581 A1 | 10/2019 | Doshi et al. | |

FOREIGN PATENT DOCUMENTS

| | | | |
|---|---|---|---|
| EP | 3429513 A1 | 1/2019 | |
| GB | 2123300 A * | 2/1984 | ............ A61B 5/204 |
| WO | 0108106 A2 | 2/2001 | |
| WO | 2015031389 A2 | 3/2015 | |
| WO | 2015058114 A1 | 4/2015 | |
| WO | 2017161331 A1 | 9/2017 | |

OTHER PUBLICATIONS

Amendola, Marco A., Banner, Marc P., Pollack, Howard M., Gordon, Roy L.; Fluoroscopically Guided Pyeloureteral Interventions by Using a Perurethral Transvesical Approach; American Journal of Roentgenology; Jan. 1989; vol. 152(1); pp. 97-102; 10.2214/ajr. 152.1.97.

Tainhong Dai et al.—"Ultraviolet C irradiation: an alternative antimicrobial approach to localized infections?"—Expert Review of Anti-infective Therapy—Feb. 2012—vol. 10 Issue 2—pp. 185-195—United States—Available from Internet <URL: https://www.ncbi.nlm.nih.gov/pmc/articles/PMC3292282/>.

Dr. J. Stephen Guffey et al.—"In Vitro Bactericidal Effects of 405-nm and 470-nm Blue Light"—Photomedicine and Laser Surgery—Jan. 2, 2007—vol. 24 Issue 6—pp. 684-688—United States—Available from Internet <URL: https://pubmed.ncbi.nlm.nih.gov/17199466/>.

Priyadarshini Singha et al.—"A Review of the Recent Advances in Antimicrobial Coatings for Urinary Catheters"—Acta Biomater—Mar. 1, 2017—vol. 50—pp. 20-40—United States—Available from Internet <URL: https://pubmed.ncbi.nlm.nih.gov/27916738/>.

Manaf Al-Qahtani et al.—"Efficacy of anti-microbial catheters in preventing catheter associated urinary tract Infections in hospitalized patients: A review on recent updates"—Journal of Infection and Public Health—Sep. 15, 2019—vol. 12 Issue 6—pp. 760-766—United States—Available from Internet <URL: https://pubmed.ncbi.nlm.nih.gov/31628048/>.

Yvonee J. Cortese et al.—"Review of Catheter-Associated Urinary Tract Infections and In Vitro Urinary Tract Models"—Journal of Healthcare Engineering—Oct. 14, 2018—vol. 2018—United States—Available from Internet <URL: https://pubmed.ncbi.nlm.nih.gov/30405898/>.

* cited by examiner

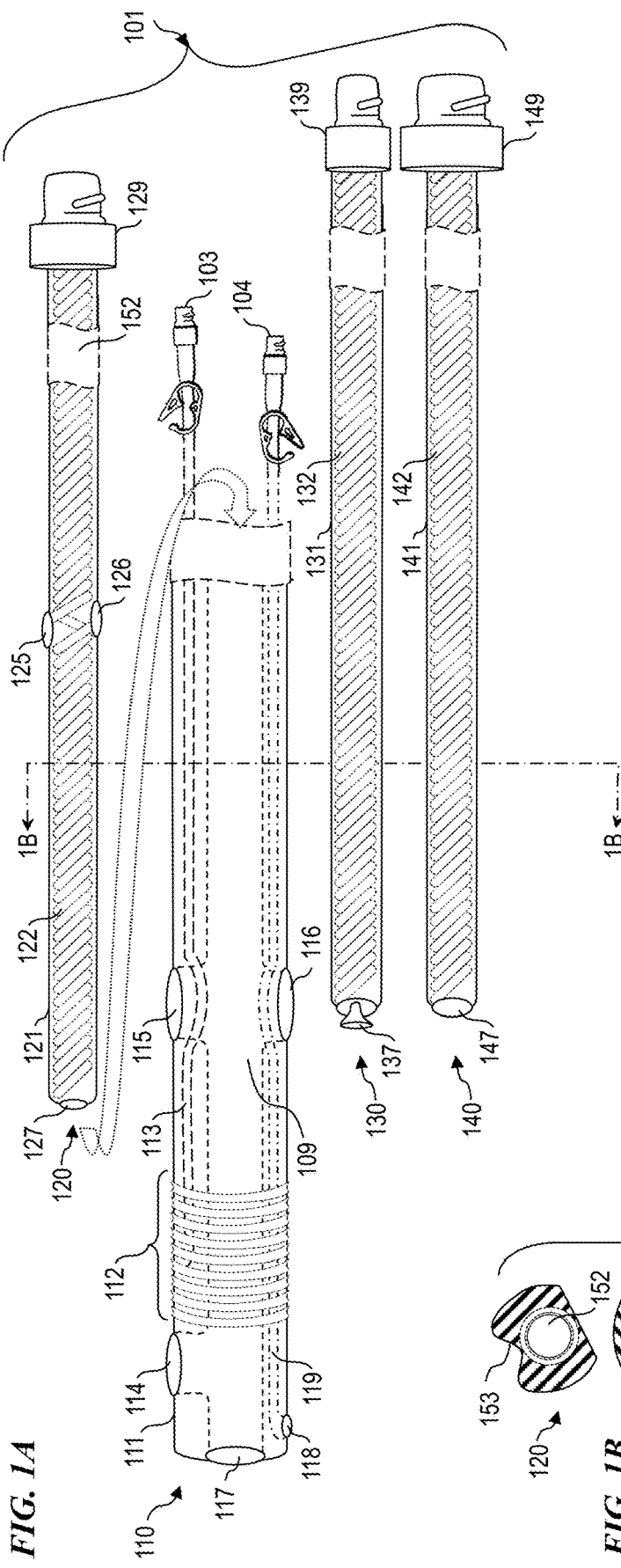

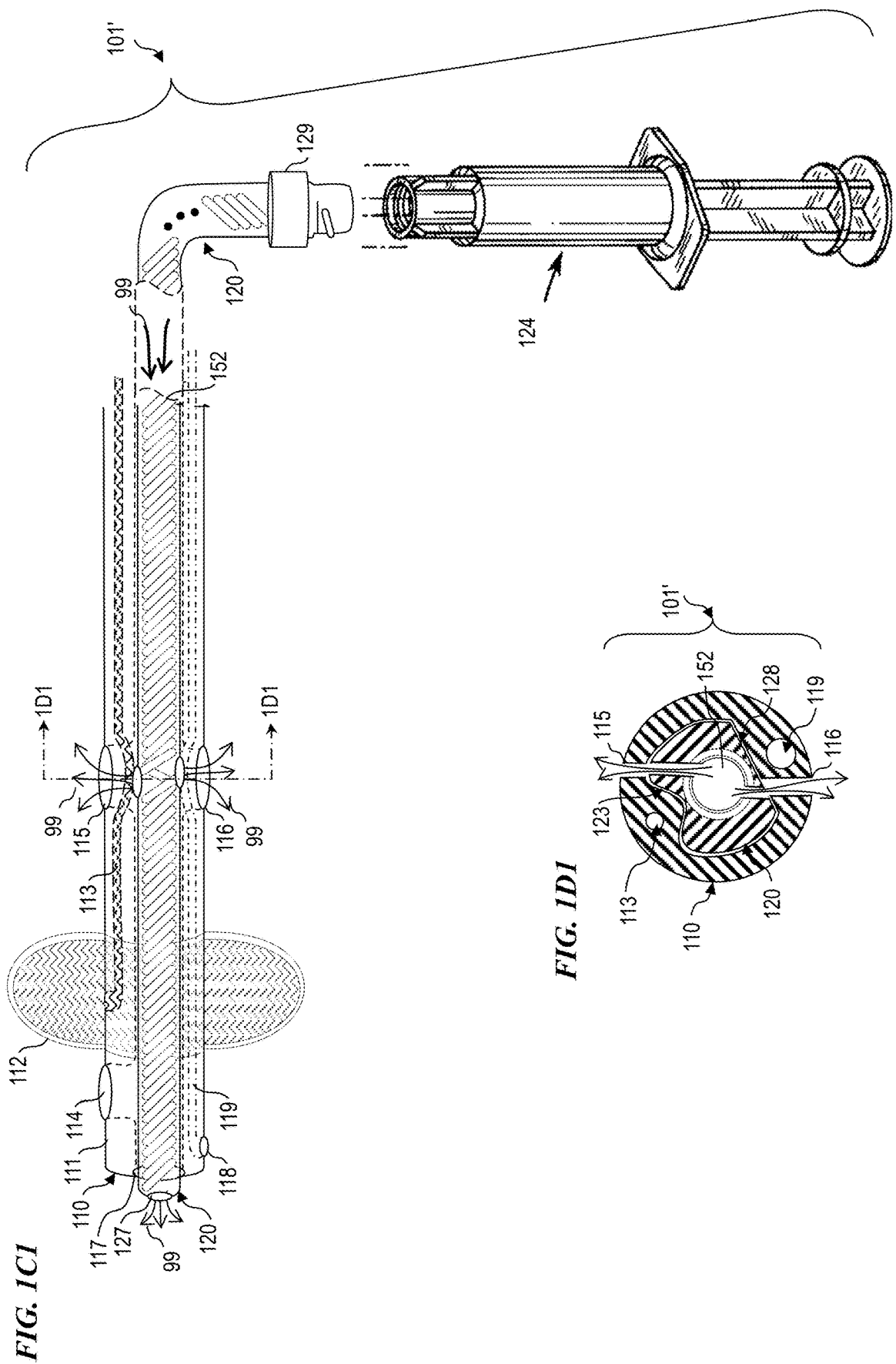

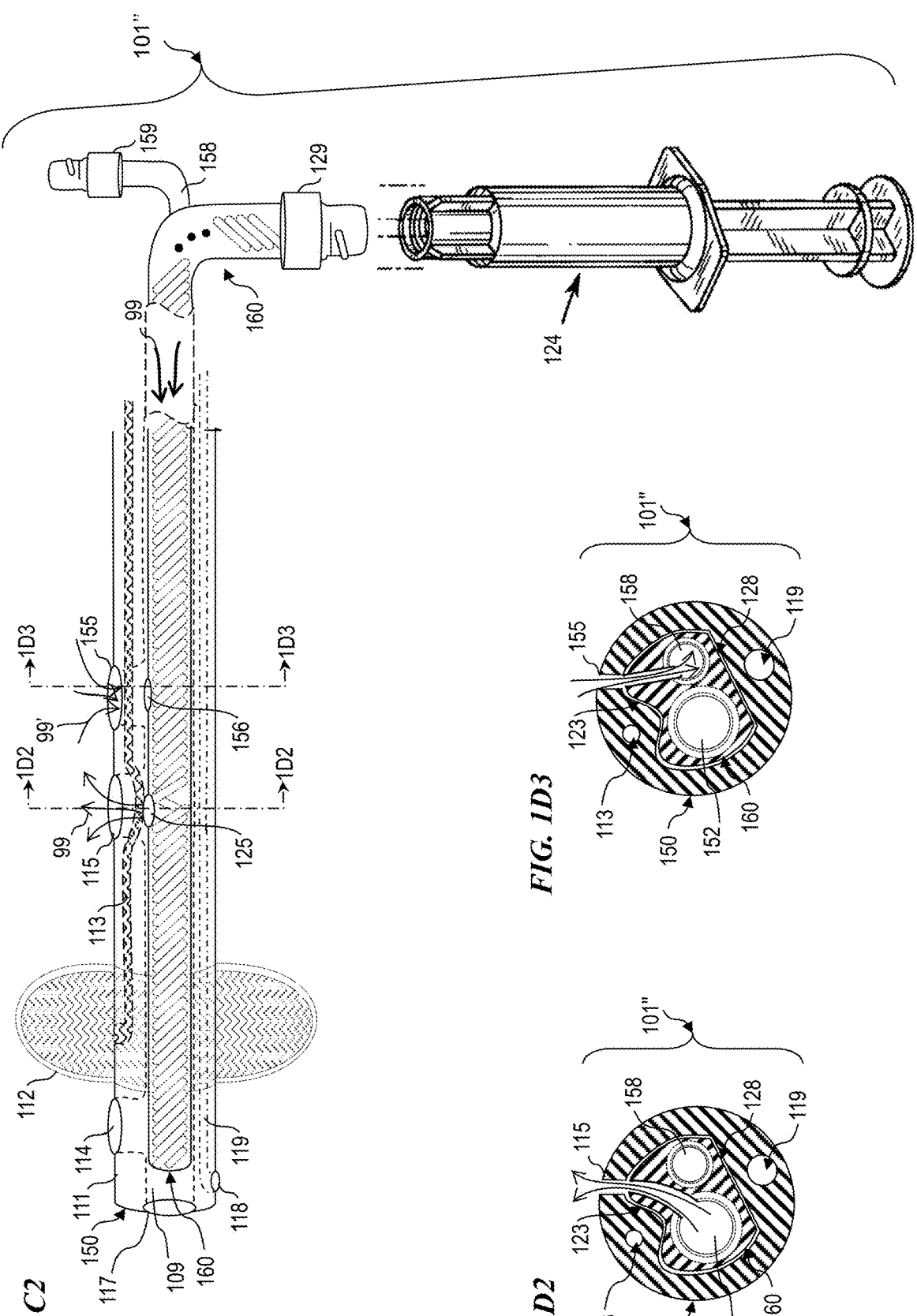

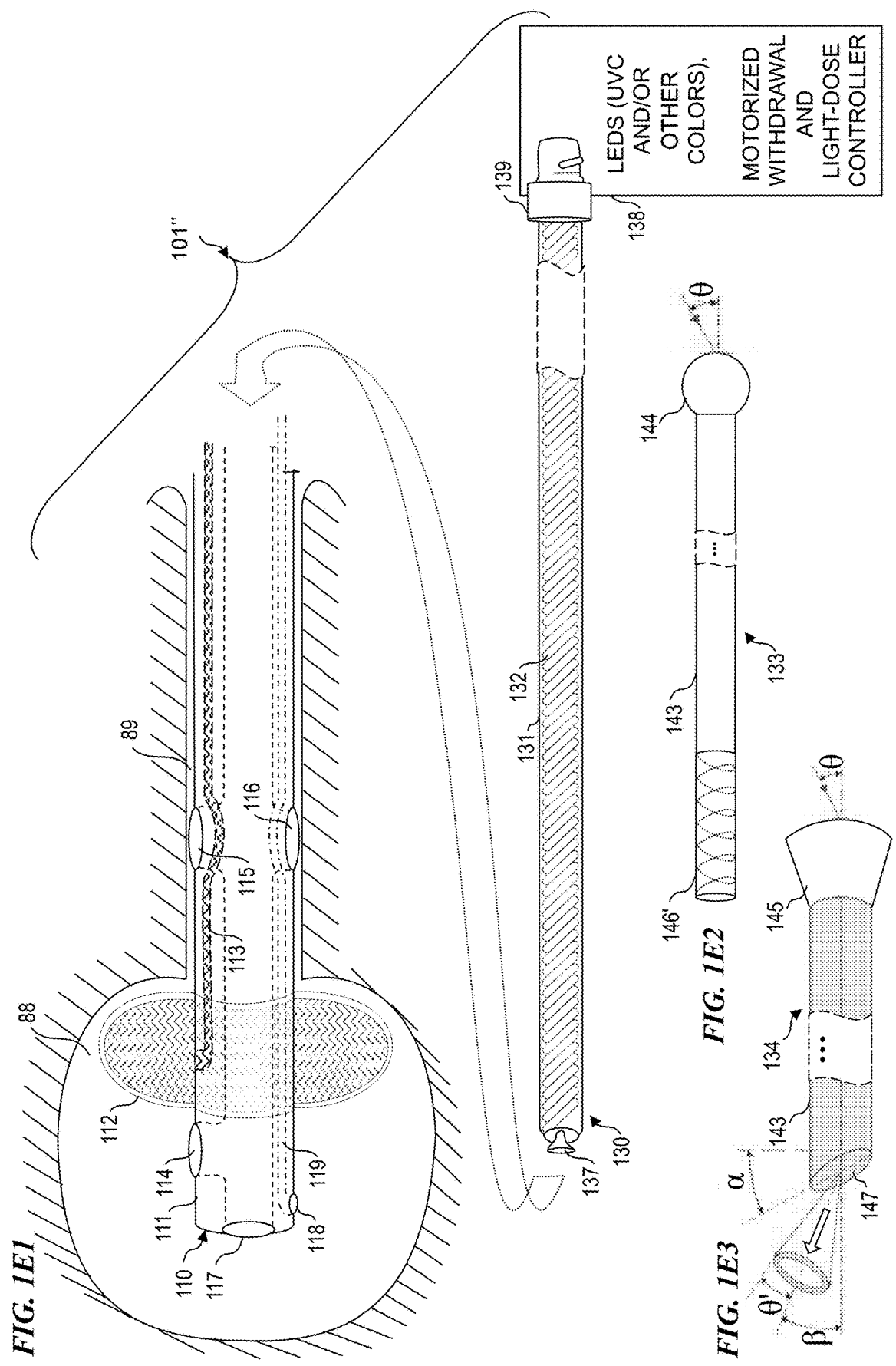

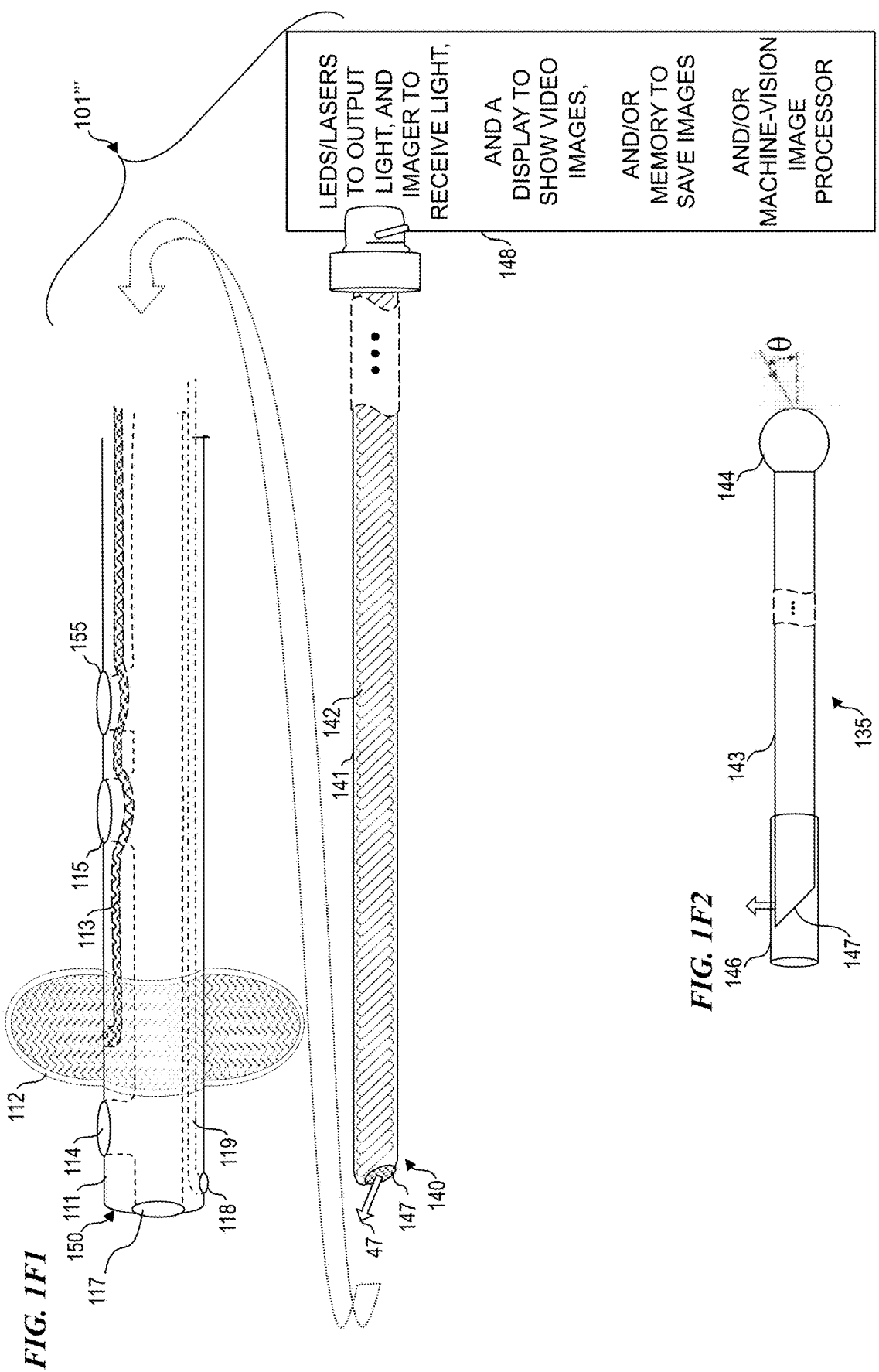

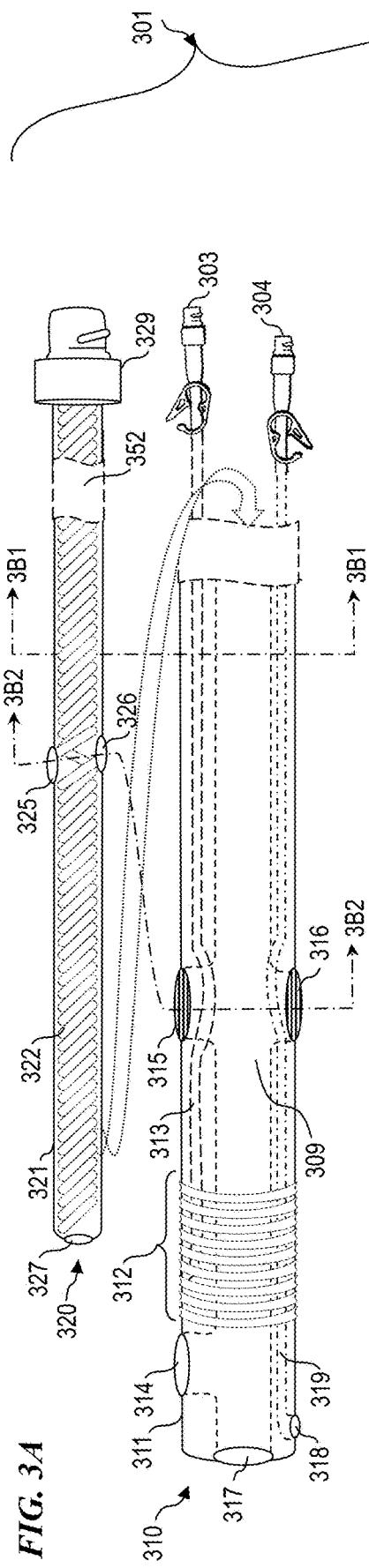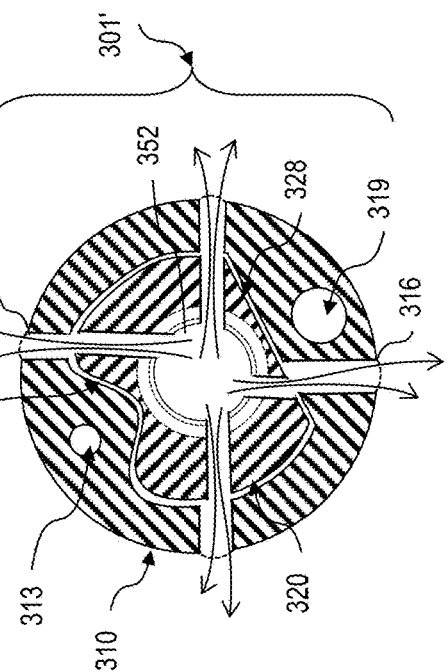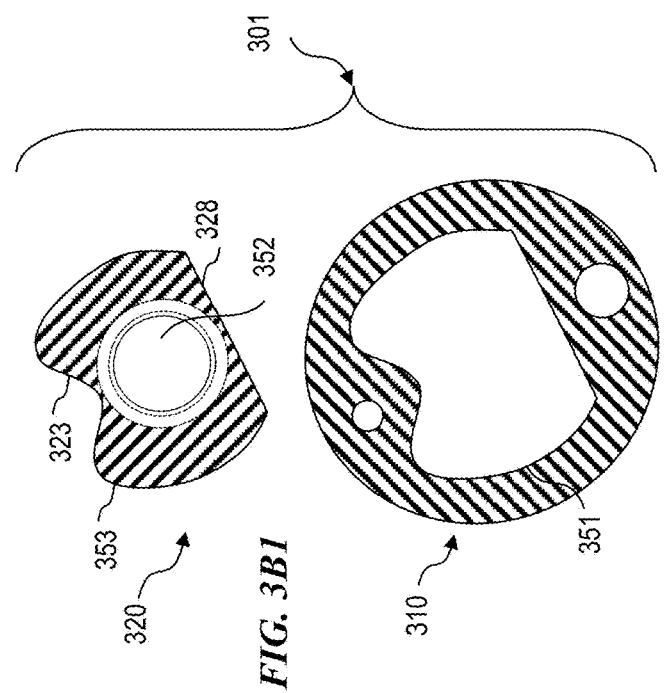

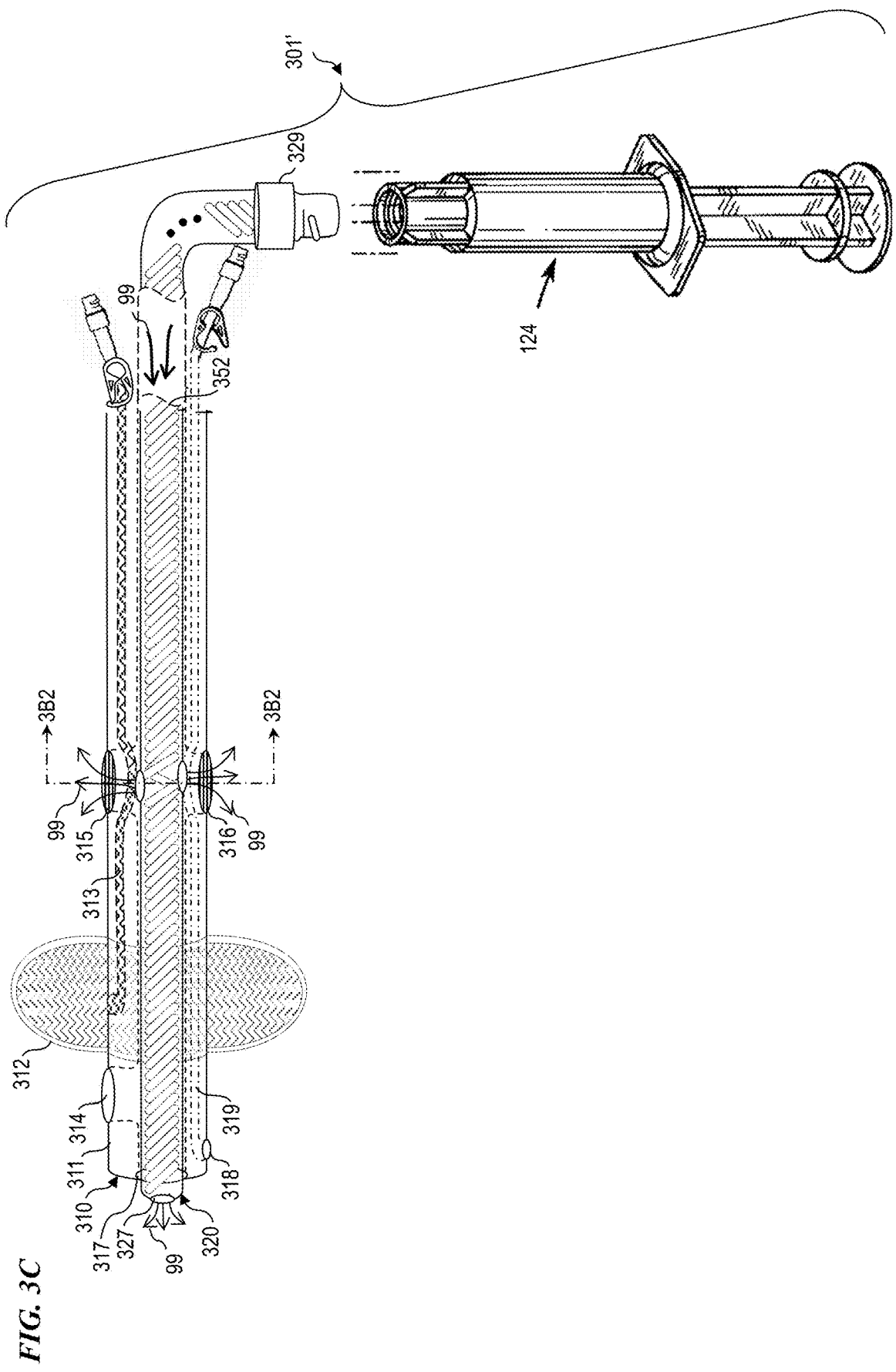

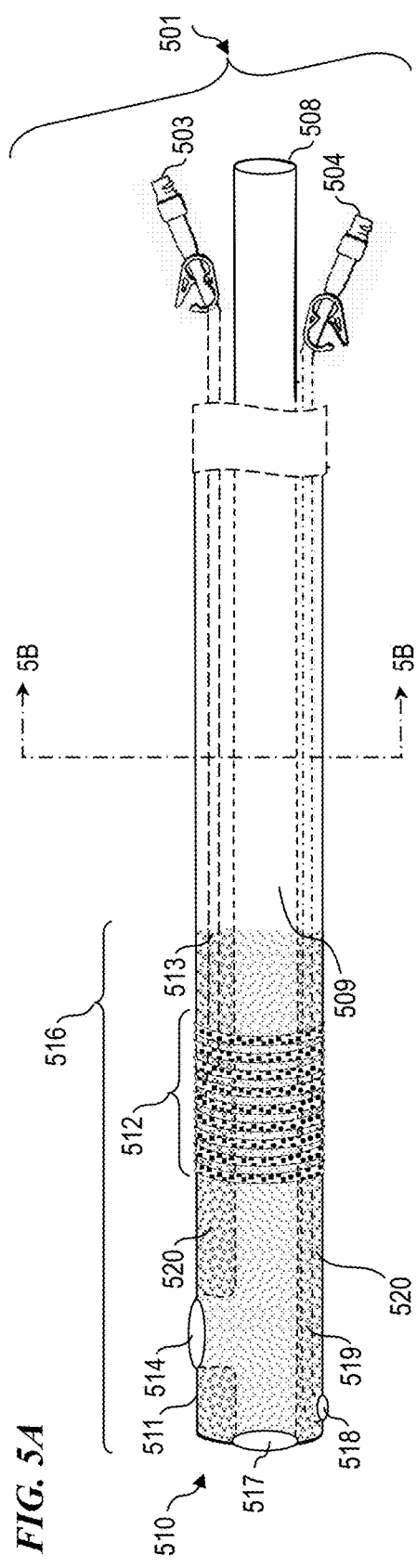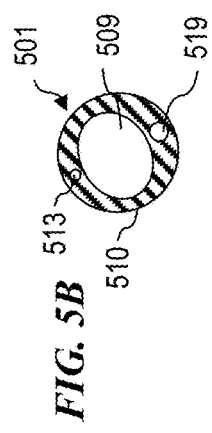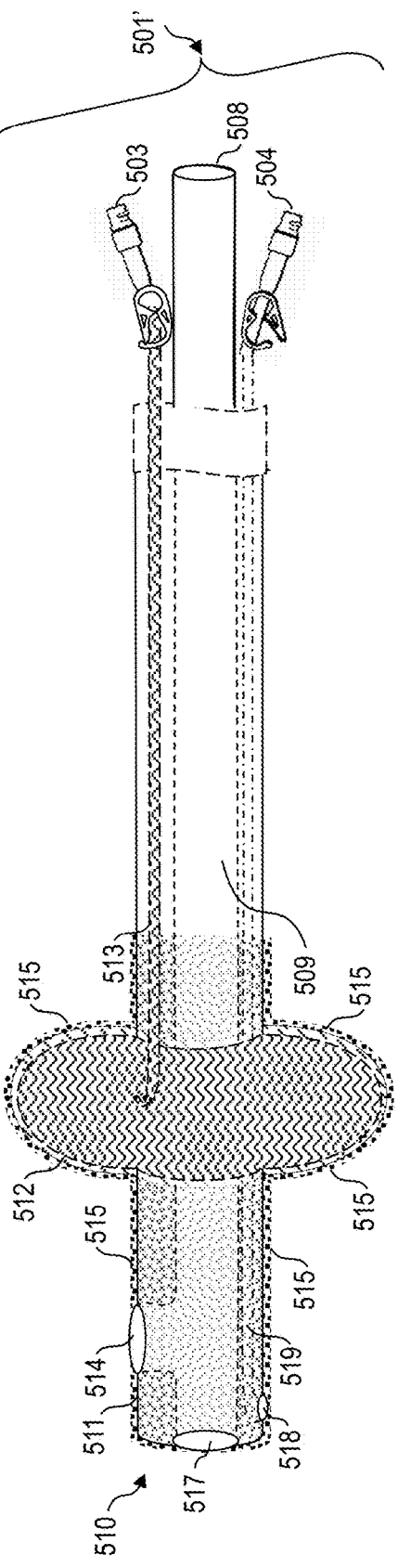

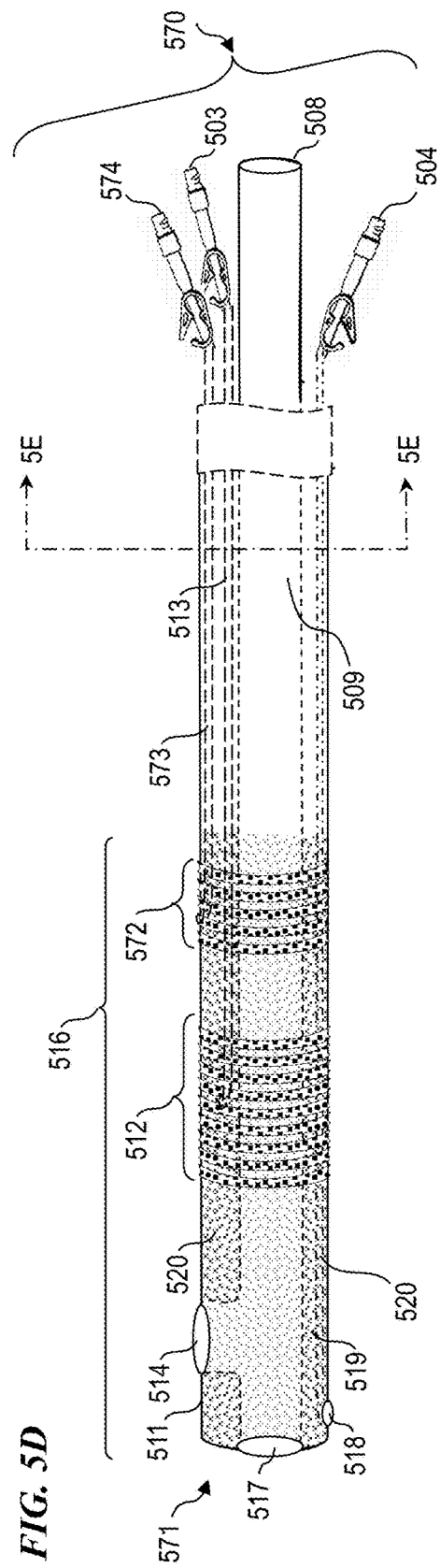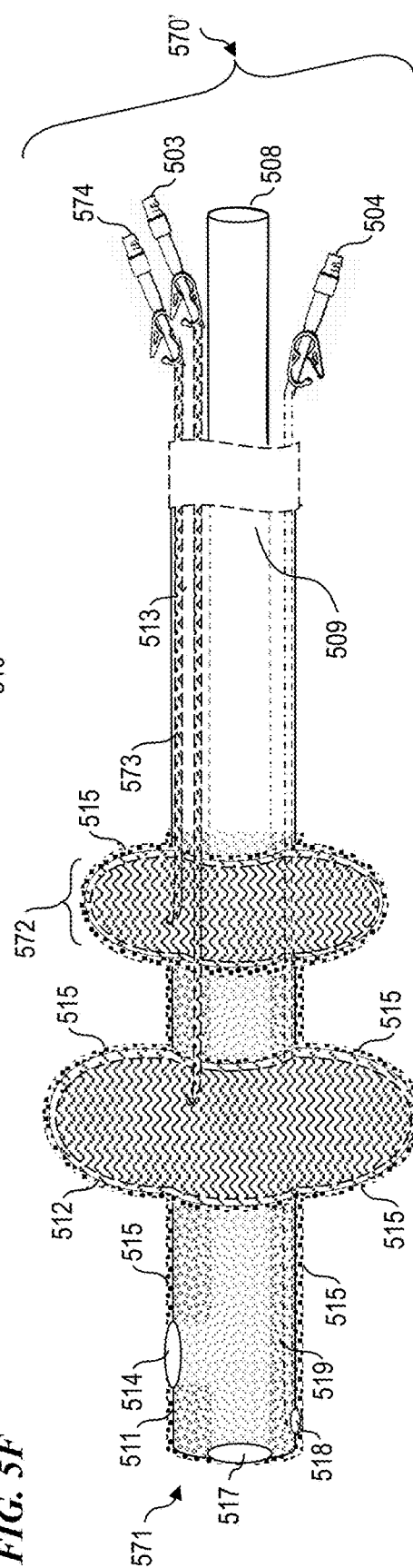
FIG. 5D
FIG. 5E
FIG. 5F

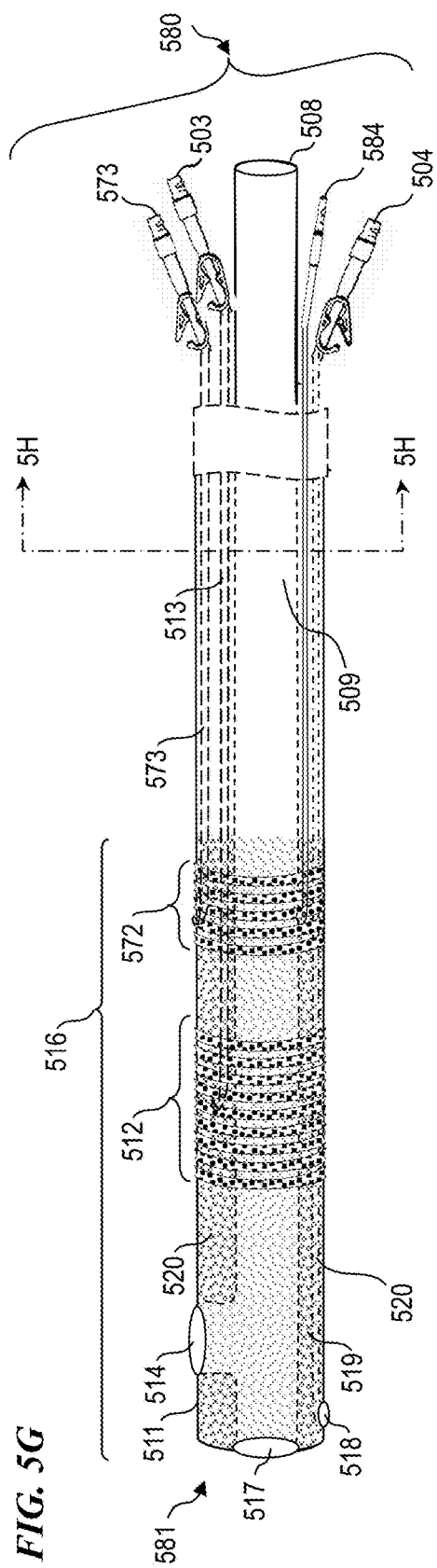
FIG. 5G
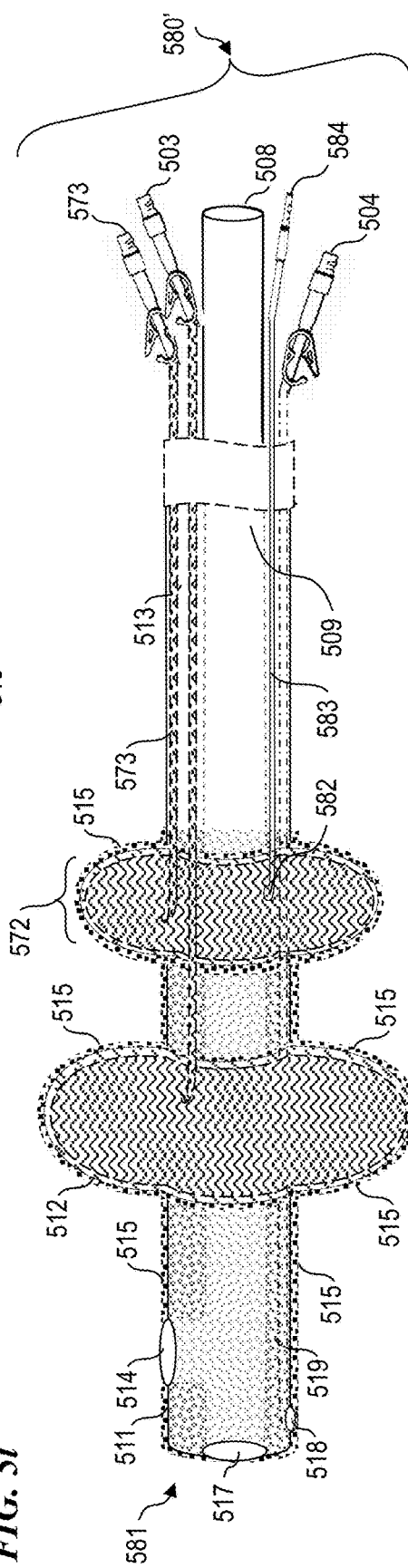
FIG. 5H
FIG. 5i

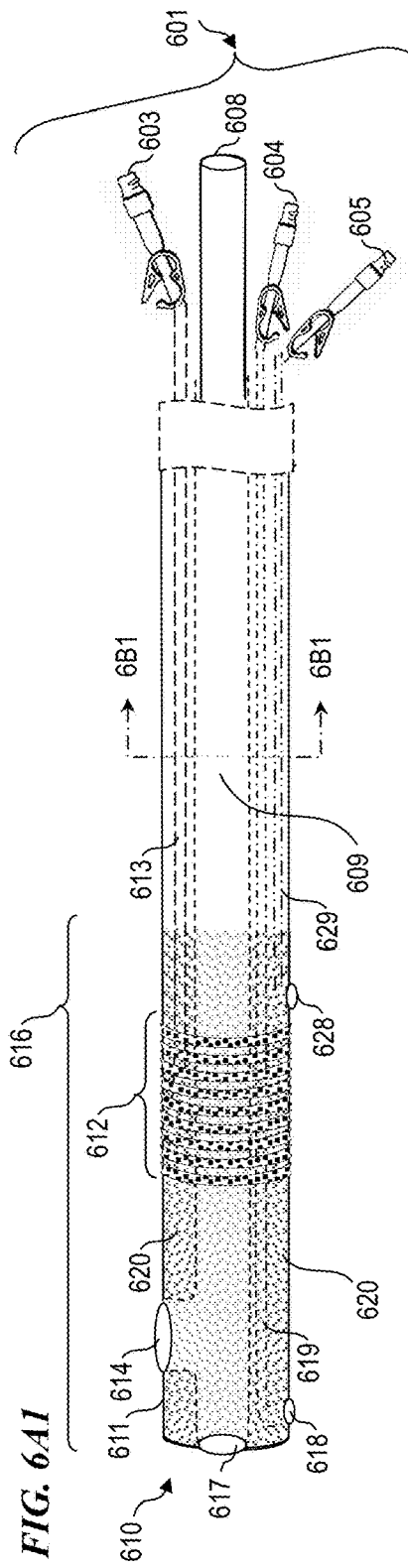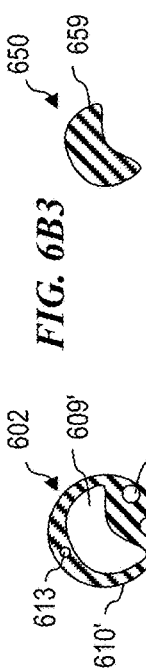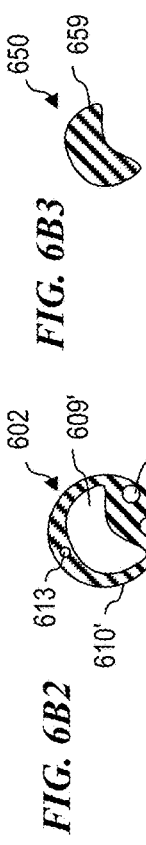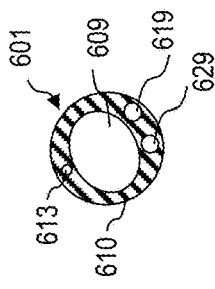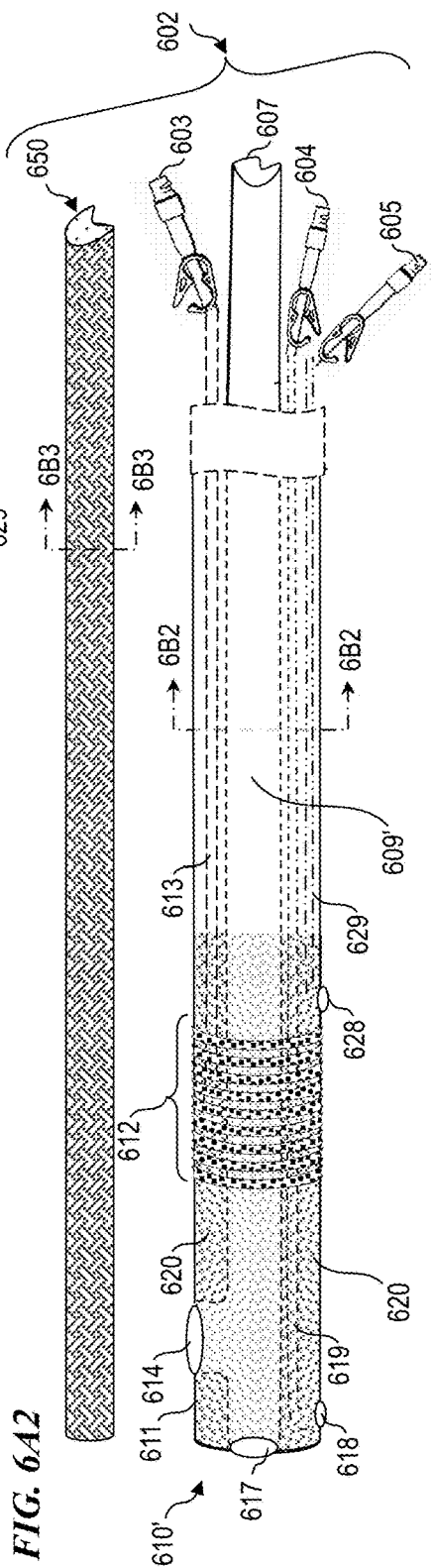

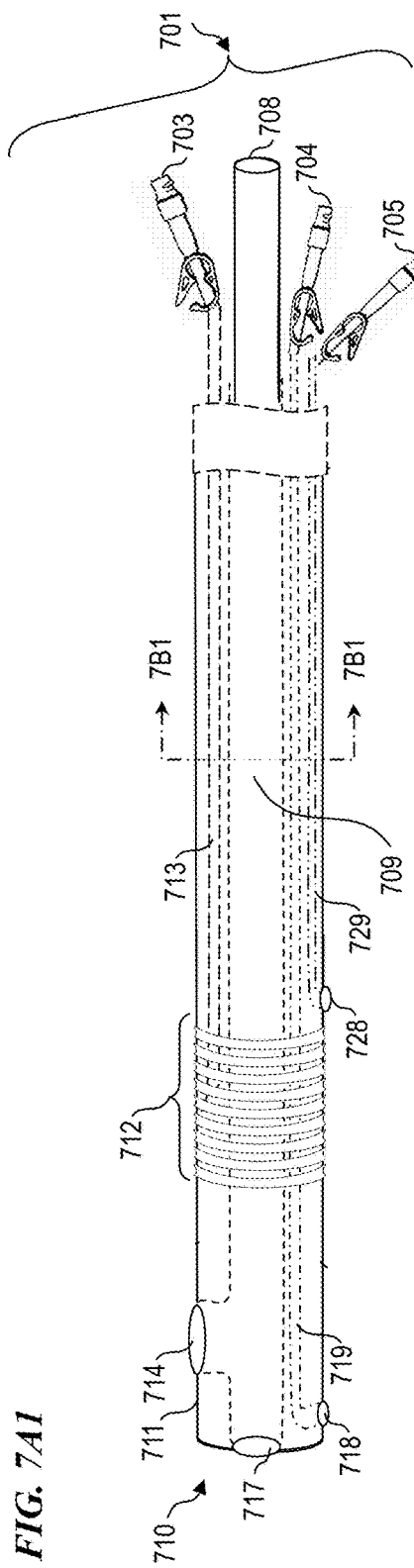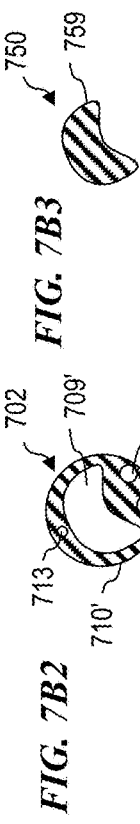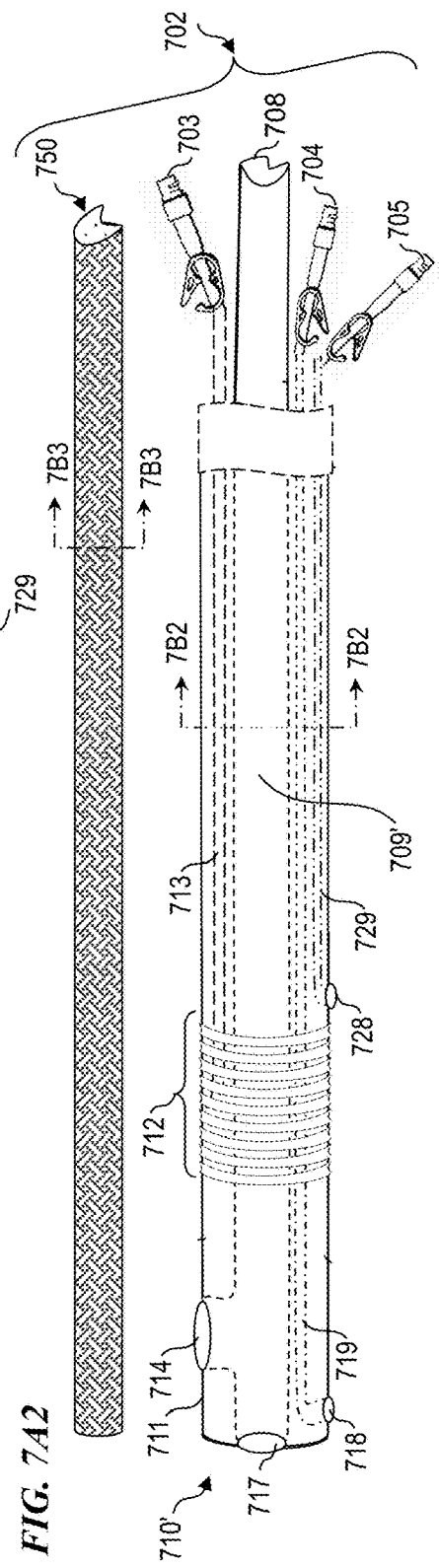

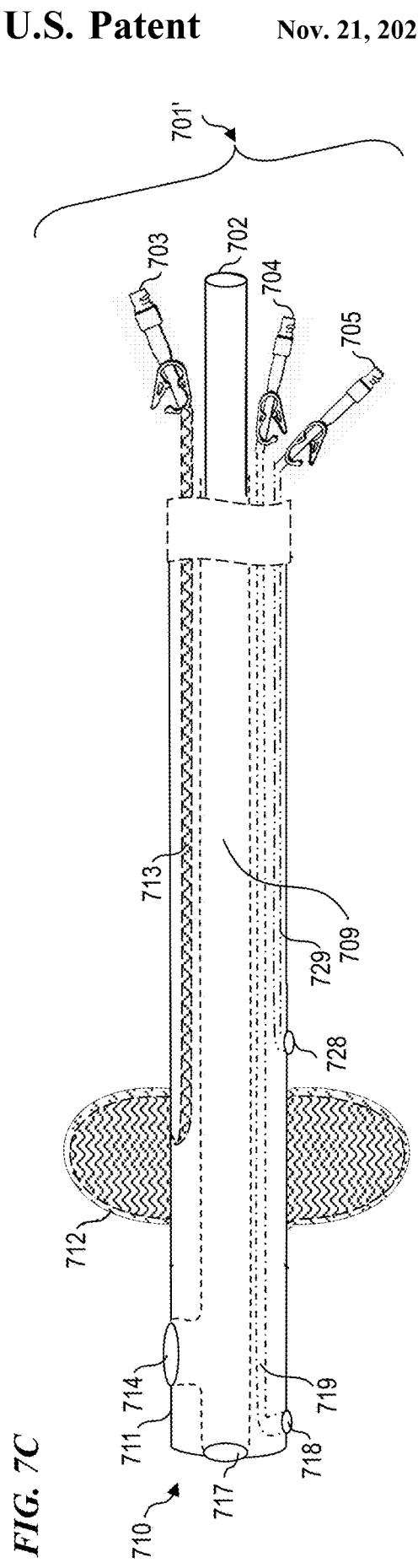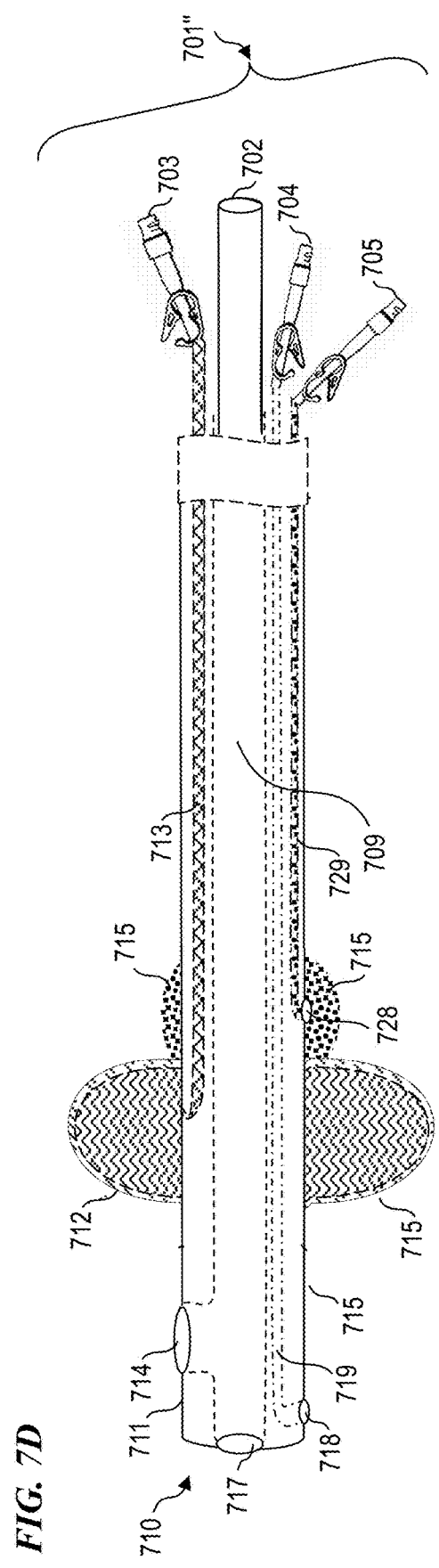

METHOD AND APPARATUS FOR TREATING GENITOURINARY PROBLEMS

CROSS-REFERENCE TO RELATED APPLICATIONS

This application claims the benefit of U.S. Provisional Patent Application No. 62/916,191; filed Oct. 16, 2019; entitled APPARATUS AND METHOD FOR TREATING GENITOURINARY PROBLEMS.

This application claims the benefit of U.S. Provisional Patent Application No. 62/965,721; filed Jan. 24, 2020; entitled APPARATUS AND METHOD FOR TREATING GENITOURINARY PROBLEMS.

FIELD OF THE INVENTION

This invention relates to the field of medical treatment, and more specifically to a method and apparatus for treating genitourinary (e.g., ureter, bladder, and/or urethra) problems with a urinary catheter that inhibits bleeding and infections. Some embodiments include a urinary catheter having a coating that has a hemostatic (anti-bleeding) medicament that is activated by contact with urine or water and has anti-infection (e.g., prevents formation of bacterial film) properties. Some embodiments include a flexible Foley-type catheter and a stiffer sheath that is insertable into and removable from the catheter, wherein the sheath and the catheter each have ports that are align-able to one another for depositing a hemostatic (anti-bleeding) medicament at a location of bleeding in the urethra and/or bladder and/or ureters, and optionally for rinsing the medicament away. In some embodiments, the catheter includes a light-guide structure, such as a polymeric optical fiber, for delivering ultraviolet light having wavelengths and intensities effective at controlling microbial infections in the urethra and/or bladder and/or ureters of a patient.

BACKGROUND OF THE INVENTION

Treatments of certain ailments of the urinary tract, such as radiation treatment of cancers in the area, can cause bleeding that is difficult to control. Foley catheters are often inserted through the urethra into the bladder, and a small balloon at the bladder end of the catheter is filled with, for example, saline to keep the catheter from coming out. Attempts to inject a hemostatic (anti-bleeding) medicament into a conventional Foley catheter typically results in the medicament exiting the catheter at the proximal end rather than propagating to the desired location in the urethra and/or bladder due to the flexible stretchable nature of the conventional Foley catheter.

An article by Tianhong Dai, et al. titled "Ultraviolet C irradiation: an alternative antimicrobial approach to localized infections?" (*Expert Rev Anti Infect Ther.* 2012 February; 10(2): 185-195. doi:10.1586/eri.11.166.) notes the following: "Ultraviolet (UV) irradiation is electromagnetic irradiation with a wavelength (100-400 nm)—shorter than that of visible light (400-700 nm), but longer than x-rays (<100 nm). UV irradiation is divided into four distinct spectral areas including vacuum UV (100-200 nm), UVC (200-280 nm), UVB (280-315 nm) and UVA (315-400 nm) . . . . The UVC doses required to inactivate a therapeutically sufficient fraction of microorganisms in vivo (e.g., 180 s irradiation time in study of Thai et al. (Thai TP, Keast DH, Campbell KE, Woodbury MG, Houghton PE. "Effect of ultraviolet light C on bacterial colonization in chronic wounds." *Ostomy Wound Manage.* 2005; 51(10):32-45. "Important clinical study showing the efficacy of UVC in treating chronic bacterial infections in pressure ulcers." [PubMed: 16230765])) may be orders of magnitude higher than those for in vitro (e.g., 5 s irradiation time in the study of Conner-Kerr et al. (Conner-Kerr TA, Sullivan PK, Gaillard J, Franklin ME, Jones RM. "The effects of ultraviolet radiation on antibiotic-resistant bacteria in vitro." *Ostomy Wound Manage.* 1998; 44(10):50-56. "Important study demonstrated that antibiotic-resistant bacteria are sensitive to ultraviolet C(UVC) inactivation." [PubMed: 9866596])). This is because the energy of UVC irradiation attenuates exponentially when penetrating into tissue. One advantage of using UVC over antibiotics is that UVC can eradicate microorganisms in a much faster manner (2-3-$\log_{10}$ eradication of microorganism population in vivo could be achieved in less than 1 h), while antibiotics usually take several days to take effect, especially in burns and chronic wounds that frequently have impaired blood perfusion. UVC may also be much more cost effective than the commonly used antibiotics. . . . Studies found that UVC at the effective antimicrobial doses can cause DNA damage to mammalian cells to some extent. However, it has also been found that the UVC-induced DNA damages can be rapidly repaired by the DNA repairing enzymes. In contrast to the large amount of studies regarding the chronic effects of UVB on human skin and tissue, there has been no similar report on the chronic effects of UVC. However, it has been suggested in an animal study that UVC is less carcinogenic than UVB because of its more superficial penetration depth. (Sterenborg HJ, van der Putte SC, van der Leun JC. "The dose—response relationship of tumorigenesis by ultraviolet radiation of 254 nm." *Photochem Photobiol.* 1988; 47(2):245-253. Reported that UVC is less carcinogenic to mouse skin than ultraviolet B. [PubMed: 3344292]) The authors of this paper state that, 'Abnormal differentiation of a layer of cells that is committed to being sloughed off anyway (UVC) is not harmful, whereas mutation of the basal cells (UVA or UVB) may result in skin cancer.' On the other hand, it has been reported that UVB treatment is an effective [option] for a large number of cutaneous disorders in humans with excellent safety profiles."

An article titled "In Vitro Bactericidal Effects of 405-nm and 470-nm Blue Light" by Dr. J. Stephen Guffey, and Jay Wilborn (Published Online: 2 Jan. 2007 at website doi.org/10.1089/pho.2006.24.684; Photomedicine and Laser Surgery, VOL. 24, NO. 6) describes the following: "Objective: The aim of this study was to determine the bactericidal effect of 405- and 470-nm light on two bacteria, *Staphylococcus aureus* and *Pseudomonas aeruginosa*, in vitro. Background Data: It is well-known that UV light kills bacteria, but the bactericidal effects of UV may not be unique since recent studies indicate that blue light produces a somewhat similar effect. The effects of blue light seem varied depending on wavelength, dose and the nature of the bacteria, hence this study. Methods: Two common aerobes, *Staphylococcus aureus* and *Pseudomonas aeruginosa*, and anaerobic *Propionibacterium acnes* were tested. Each organism was treated with Super Luminous Diode probes with peak emission at 405 and 470 nm. Treatment was timed to yield 1, 3, 5, 10, and 15 Jcm-2 doses. Colony counts were performed and compared to untreated controls. Results: The 405-nm light produced a dose dependent bactericidal effect on *Pseudomonas aeruginosa* and *Staphylococcus aureus* (p<0.05), achieving as much as 95.1% and nearly 90% kill rate for each, respectively. The 470-nm light effectively killed *Pseudomonas aeruginosa* at all dose levels, but only killed

*Staphylococcus aureus* at 10 and 15 J cm$^{-2}$. With this wavelength, as much as 96.5% and 62% reduction of *Pseudomonas aeruginosa* and *Staphylococcus aureus* was achieved, respectively. Neither of the two wavelengths proved bactericidal with anaerobic *Propionibacterium acnes*. Conclusion: The results indicate that, in vitro, 405- and 470-nm blue light produce dose dependent bactericidal effects on *Pseudomonas aeruginosa* and *Staphylococcus aureus* but not *Propionibacterium acnes*."

An article titled "A Review of the Recent Advances in Antimicrobial Coatings for Urinary Catheters," by Priyadarshini Singha, Jason Locklin, and Hitesh Handa (Acta Biomater. 2017 Mar. 1; 50: 20-40. Published online 2016 Dec 1. doi: 10.1016/j.actbio.2016.11.070; PMCID: PMC5316300; NIHMSID: NIHMS837082; PMID: 27916738) describes the following: "More than 75% of hospital-acquired or nosocomial urinary tract infections are initiated by urinary catheters, which are used during the treatment of 15-25% of hospitalized patients. Among other purposes, urinary catheters are primarily used for draining urine after surgeries and for urinary incontinence. During catheter-associated urinary tract infections, bacteria travel up to the bladder and cause infection. A major cause of catheter-associated urinary tract infection is attributed to the use of non-ideal materials in the fabrication of urinary catheters. Such materials allow for the colonization of microorganisms, leading to bacteriuria and infection, depending on the severity of symptoms. The ideal urinary catheter is made out of materials that are biocompatible, antimicrobial, and antifouling. Although an abundance of research has been conducted over the last forty-five years on the subject, the ideal biomaterial, especially for long-term catheterization of more than a month, has yet to be developed. The aim of this review is to highlight the recent advances (over the past 10 years) in developing antimicrobial materials for urinary catheters and to outline future requirements and prospects that guide catheter materials selection and design."

An article titled "Efficacy of anti-microbial catheters in preventing catheter associated urinary tract infections in hospitalized patients: A review on recent updates" by Manaf Al-Qahtani, Abeer Safan, Ghufran Jassim, and Sara Abadla describes "Catheter-associated urinary tract infections (CAUTIs) are the common hospital-associated infections (HAIs), which can be prevented by practicing necessary precautions and by using antimicrobial urinary catheters (UCs). The efficacy of antimicrobial UCs against standard catheters for averting CAUTIs is poorly studied. The objective of the review is to analyze the efficacy of various types of antimicrobial UCs used in hospitalized patients in preventing CAUTIs. The major antimicrobial UCs are silver and antibiotic catheters, in contrast, few antimicrobial catheters include antimicrobial peptides, bactericidal enzymes, bacteriophages, and many are under clinical evaluation. The review concludes that even though many antimicrobial methods are available to prevent CAUTIs, the incidence rate is still high. Antibiotic resistance, leaching of catheter materials which may cause side effects and additional costs are the major challenges for the UCs. Further research is warranted and should focus on cost-effective and ideal antimicrobial UCs, in which the microorganisms cannot form biofilms or develop resistance."

An article titled "Review of Catheter-Associated Urinary Tract Infections and In Vitro Urinary Tract Models" by Yvonne J. Cortese, Victoria E. Wagner, Morgan Tierney, Declan Devine, and Andrew Fogarty (website: new.hindawi.com/journals/jhe/2018/2986742/) describes "Catheter-associated urinary tract infections (CAUTIs) are one of the most common nosocomial infections and can lead to numerous medical complications from the mild catheter encrustation and bladder stones to the severe septicaemia, endotoxic shock, and pyelonephritis. Catheters are one of the most commonly used medical devices in the world and can be characterized as either indwelling (ID) or intermittent catheters (IC). The primary challenges in the use of IDs are biofilm formation and encrustation. ICs are increasingly seen as a solution to the complications caused by IDs as ICs pose no risk of biofilm formation due to their short time in the body and a lower risk of bladder stone formation. Research on IDs has focused on the use of antimicrobial and antibiofilm compounds, while research on ICs has focused on preventing bacteria entering the urinary tract or coming into contact with the catheter. There is an urgent need for in vitro urinary tract models to facilitate faster research and development for CAUTI prevention. There are currently three urinary tract models that test IDs; however, there is only a single very limited model for testing ICs. There is currently no standardized urinary tract model to test the efficacies of ICs."

United States Patent 583,382 issued to Hermann Wulfing Lüer on May 25, 1897 with the title "Syringe," and is incorporated herein by reference.

U.S. Pat. No. 5,702,373 to Samson issued to Dec. 30, 1997 with the title "Composite super-elastic alloy braid reinforced catheter," and is incorporated herein by reference. U.S. Pat. No. 5,702,373 describes a composite catheter assembly suitable for accessing a tissue target within the body, typically a target which is accessible through the vascular system. Central to the U.S. Pat. No. 5,702,373 invention is the presence in the catheter assembly of a catheter section having a braided metallic reinforcing member, typically of super-elastic alloy ribbon, situated within the reinforced catheter section in such a way to create a catheter having an exceptionally thin wall, controlled stiffness, high resistance to kinking, and complete recovery in vivo from kinking situations. The braid may have a single pitch or may vary in pitch along the axis of the catheter or catheter section. The braided ribbon reinforcing member typically is placed between a flexible outer tubing member and an inner tubing member to produce a catheter section which is very flexible but highly kink resistant. At least a proximal portion or section of the catheter assembly is a section made of a stiff polymeric or metallic tubing member.

U.S. Pat. No. 6,165,127 issued to Crowley on Dec. 26, 2000 with the title "Acoustic imaging catheter and the like," and is incorporated herein by reference. U.S. Pat. No. 6,165,127 describes acoustic imaging balloon catheters formed by a disposable liquid-confining sheath supporting a high fidelity, flexible drive shaft which carries on its end an ultrasound transducer and includes an inflatable dilatation balloon. The shaft and transducer rotate with sufficient speed and fidelity to produce real time images on a TV screen. In preferred embodiments, special features that contribute to the high fidelity of the drive shaft include the particular multi-filar construction of concentric, oppositely wound, interfering coils, a pre-loaded torque condition on the coils enhancing their interfering contact, and dynamic loading of the distal end of the probe, preferably with viscous drag. The coil rotating in the presence of liquid in the sheath is used to produce a desirable pressure in the region of the transducer. Numerous selectable catheter sheaths are shown including a sheath with an integral acoustically-transparent window, sheaths with end extensions that aid in positioning, a liquid injection-producing sheath, a sheath having its window section under tension employing an axially loaded bearing, a sheath carrying a dilatation or positioning balloon over the transducer, a sheath carrying a distal rotating surgical tool and a sheath used in conjunction with a side-viewing trocar.

U.S. Pat. No. 6,527,737 issued to Kaneshige on Mar. 4, 2003 with the title "Indwelling urethra catheter," and is incorporated herein by reference. U.S. Pat. No. 6,527,737 describes an indwelling catheter that includes a flexible "malecot" tube having a plurality of slits elongating toward the longitudinal direction in the vicinity of the tip of the catheter, a flexible core wire movable in the axial direction along the malecot tube with its tip fixed to the tip of the malecot tube, a cylindrical connector fixed to the root side of the malecot tube and permitting the root of the core wire to protrude out of the end portion of the malecot tube, and a stopper provided on the connector to constrain arbitrary movement of the core wire.

U.S. Pat. No. 6,898,454 issued to Atalar, et al. on May 24, 2005 with the title "Systems and methods for evaluating the urethra and the periurethral tissues," and is incorporated herein by reference. U.S. Pat. No. 6,898,454 describes systems and methods for the evaluation of the urethra and periurethral tissues using an MRI coil adapted for insertion into the male, female or pediatric urethra. The MRI coil may be in electrical communication with an interface circuit made up of a tuning-matching circuit, a decoupling circuit and a balun circuit. The interface circuit may also be in electrical communication with an MRI machine. In certain practices, the U.S. Pat. No. 6,898,454 invention provides methods for the diagnosis and treatment of conditions involving the urethra and periurethral tissues, including disorders of the female pelvic floor, conditions of the prostate and anomalies of the pediatric pelvis.

U.S. Pat. No. 7,613,478 issued to Jabri et al. on Nov. 3, 2009 with the title "Method and system for portability of clinical images using a high-quality display and portable device," and is incorporated herein by reference. U.S. Pat. No. 7,613,478 describes a method and system for improved clinical workflow using wireless communication. A system for remote image display includes a data source with image data, wherein the data source is capable of transmitting the image data. The system also includes an identifiable display device capable of displaying image data transferred from the data source and a portable device capable of identifying the display device and requesting image data transfer from the data source to the display device without the transfer of the image data between the portable device and the data source. The system may also include an access point for relaying communication between the portable device and the data source. Communication between the portable device, the data source, and/or the display may include wireless communication.

U.S. Pat. No. 9,474,811 to Sharma issued on Oct. 25, 2016 with the title "Method of treating an eye infection using electromagnetic radiation in the UVC," and is incorporated herein by reference. U.S. Pat. No. 9,474,811 describes that infections of body tissues, particularly of the eye or of wounds, are treated by brief low-intensity irradiation with ultraviolet radiation in the UVC band. A suitable treatment device contains a light-emitting diode producing UVC radiation at a wavelength of about 265 nm, at a power output of 5 mW, directed on to a zone of tissue about 4 mm in diameter. An optical aiming system indicates the zone of tissue to be irradiated. Irradiation for periods as brief as 1 second has been found effective, which equates to a dose of 4 mJ/cm$^2$ delivered to the tissue. Longer periods and higher intensities may be used for more resistant infections. Such irradiation may be delivered endoscopically to treat internal infections or to prevent infection during surgery. The device may be hand held or mounted to an ophthalmic slit lamp or other support.

U.S. Pat. No. 8,409,172 issued to Moll et al. on Apr. 2, 2013 with the title "Systems and methods for performing minimally invasive procedures," and is incorporated herein by reference. U.S. Pat. No. 8,409,172 describes a robotic surgical system that includes an instrument driver and an instrument assembly operatively coupled to the instrument driver such that mechanisms of the instrument driver operate or control movement, operation, or both, of components of the instrument assembly. The instrument assembly components include an elongate flexible guide instrument, an optical light source, a camera and a working tool, wherein the light source, camera, and working tool are carried in one or more lumens of the guide instrument. An operator control station is operatively coupled to the instrument driver via a remote communication link. The instrument assembly further includes an inflatable visualization balloon carried on a distal end portion of the guide instrument, the light source and camera having distal ends located within an interior of the balloon, the balloon comprising a lumen extending from the guide instrument to a distal facing wall of the balloon, such that the working instrument may extend from a respective lumen of the guide instrument through the balloon lumen to contact body tissue when the distal end of the guide instrument is positioned in an interior body region.

U.S. Pat. No. 8,784,461 issued to Webb et al. on Jul. 22, 2014 with the title "Method and apparatus for optical stimulation of nerves and other animal tissue," and is incorporated herein by reference. U.S. Pat. No. 8,784,461 describes a hand-held self-contained nerve-stimulation device and method using light to provide a source of precise stimulation on one or more nerve fibers. In some embodiments, this simulation is provided through a device and method wherein a laser- or LED-light source is mounted to the handpiece. Light is passed from the light source through optical tip to simulate nerves. In some embodiments, the device is constructed from non-magnetic material such as glass, plastic or ceramics. In some embodiments, the light emanating from the optical tip can be controlled manually or automatically. In some embodiments, the handpiece contains a self-contained power source, such as batteries. In some embodiments, the handpiece is at least in part, activated by remote control in order to prevent moving the handpiece during activation. Some embodiments include a unit operable to sense a response of nerve stimulation and to suppress a laser-ablation surgery operation.

U.S. Pat. No. 9,125,573 issued to Koyrakh et al. on Sep. 8, 2015 with the title "Electrically transparent introducer sheath," and is incorporated herein by reference. U.S. Pat. No. 10,022,183 describes an introducer sheath for a medical device. The sheath includes a deformable, elongate body disposed about a longitudinal axis. The body has proximal and distal ends and defines a lumen extending between the proximal and distal ends and configured to allow passage of the medical device therethrough. The body is configured to allow an electric current to pass radially between a space outside of the body and the lumen such that the position of the medical device within a patient can be monitored and electrogram readings from body tissues can be measured while the device is in the sheath. In some embodiments of U.S. Pat. No. 10,022,183, the body may include one or more apertures extending from the radially outer surface of the body to the lumen or a portion of the body may be made from a conductive and/or fluid permeable material.

U.S. Pat. No. 9,550,005 issued to Lin et al. on Jan. 24, 2017 with the title "Systems and methods for sterilization using UV light," and is incorporated herein by reference. U.S. Pat. No. 9,550,005 describes systems, methods, and kits for sterilizing in vivo catheters using an optical fiber to deliver UV light. In an embodiment, a method for sterilizing a catheter with at least a first lumen, includes inserting a distal end of a fiber optic cable into a fiber insertion port of a catheter connector attached to a hub of the first lumen, flushing the first lumen with fluid from a fluid source, inserting the fiber optic cable into the first lumen until a stopper of the fiber optic cable is adjacent to the fiber insertion port, providing light to the fiber optic cable from a light source after the fiber optic cable is inserted into the first lumen, withdrawing the fiber optic cable from the first lumen while the light is provided, and ceasing to provide light to the fiber optic cable after the fiber optic cable is withdrawn from the first lumen. The disclosure is said to be also applicable to catheters with multiple lumens and to catheters accessed through subcutaneous ports.

U.S. Pat. No. 10,022,183 issued to Brucker et al. on Jul. 17, 2018 with the title "Temperature-responsive irrigated ablation electrode with reduced coolant flow and related methods for making and using," and is incorporated herein by reference. U.S. Pat. No. 10,022,183 describes an irrigated ablation electrode that includes a plurality of high L/d interior fluid passageways and/or slit-shaped apertures to provide for a lower rate of fluid flow and a more uniform distribution of fluid over an exterior surface of the electrode and reduce propensity for aperture blockage. In some embodiments, the slit-shaped apertures have an aspect ratio of at least three, at least five, at least ten, or at least fifteen. Some embodiments include maintaining a pressure drop of at least 345 pascals between irrigation fluid inside the irrigated ablation electrode and fluid immediately outside the electrode when the irrigation fluid has a flow rate of no more than five milliliters per minute (5 ml/min). Some embodiments include a low-density insert with a plurality of fluid channels on its exterior surface to more efficiently cool the electrode and provide a faster thermal response.

U.S. Pat. No. 10,304,188 issued to Kumar on May 28, 2019 with the title "Apparatus and method for automated cell analysis," and is incorporated herein by reference. U.S. Pat. No. 10,304,188 describes a system and method for automatically analyzing an image of cells to detect cancer. Some embodiments include eliciting and receiving a digital photomicrograph image of cells; determining a boundary of a cell in the image; identifying a plurality of characteristics of the cell from image-pixel data from within the identified boundary of the cell; reading a plurality of cell characteristics of a plurality of types of cells from a database; comparing the identified characteristics of the cells in the image to the plurality of cell characteristics read from the database; and determining a pathology based on the comparing. Some embodiments further include automatically identifying an appropriate treatment and applying the identified treatment.

United States Patent Application publication 2010/0137721 by Rose et al. published on Jun. 3, 2010 with the title "Transurethral Ultrasonic Imaging System," and is incorporated herein by reference. Publication 2010/0137721 describes an ultrasound scanning system and methods of using the same. In one preferred form, an ultrasound scanning system includes an acoustic imaging catheter comprising an ultrasonic transducer, a motion control system and an imaging computer system for imaging a patient's genitourinary system. In another preferred form, an ultrasound scanning system is used for imaging a patient's prostate gland.

European Patent EP 1210052 B1 was granted to Momich et al. on Jan. 23, 2008 with the title "Package with integrated circuit chip embedded therein and system for using same," and is incorporated herein by reference. European Patent EP 1210052 B1 describes an interactive reminder device that includes a read/write module, an integrated circuit, a power supply, memory, a clock and a prompt. The read/write module is adapted to read information stored on an identifiable integrated circuit chip and to write information onto the identifiable integrated circuit chip attached to a package. The integrated circuit is operably connected to the read/write module. The power supply is operably connected to the integrated circuit. The memory is operably connected to the integrated circuit. The clock is operably connected to the integrated circuit and the prompt is operably connected to the integrated circuit. The interactive reminder device is for use with a package having an integrated circuit chip attached thereto. The interactive reminder device is for implementing a system for prompting for the use of medication. The prompting system includes the steps of reading information stored on an integrated circuit chip regarding parameters for determining a next take time; calculating the next take time; storing a next take time in a prompting device; and prompting at the next take time. The prompting system may also be adapted for use in a health care facility wherein the steps include calculating the next take time for an identifiable patient for an identifiable medication; storing a next take time, the identified medication and the identified patient in a prompting device; prompting at the next take time; confirming that the medication integrated circuit chip is the medication integrated circuit chip associated with the identified medication; and confirming that the patient integrated circuit chip is the patient integrated circuit chip associated with the identified patient and thereafter administering the identified medication to the identified patient.

There remains a need in the art for an apparatus and method to stop bleeding and prevent or reduce infections via catheters used in lumens (such as the urethra, an artery or vein, or the intestine) of the body of humans or other animals.

SUMMARY OF THE INVENTION

The present invention provides an apparatus that includes a catheter (which, in some embodiments, includes a Foley-type catheter having an inflatable balloon portion), and a sheath-type elongated insert that is insertable into and withdrawable from the catheter, and is configured for the introduction of a medicament (such as a hemostatic (anti-bleeding) agent and/or an anti-microbial substance or the like) through the sheath to medicament-deposition exit openings in the sheath that correspond to (line up with) through-openings in the catheter once the sheath is inserted to a desired depth into the catheter, in order to deposit the medicament at a desired location of a patient's tissue (for example, a site of bleeding in a patient's urethra). In some embodiments, the shape of the inner passageway inside the Foley-type catheter is shaped ("keyed") with an asymmetric cross-sectional shape and the cross-sectional shape of the outer surface of the sheath corresponds to the inside shape of the catheter in order that the exit hole(s) in the sheath align with the through hole(s) in the catheter.

In some embodiments, the apparatus is a kit that further includes an insertable and withdrawable light-delivery sheath assembly having a light-propagation channel built into the sheath, and a source of anti-microbial light in one or more wavelength bands, including, for example, ultraviolet (UV) irradiation in the C band, called UVC light, (e.g., from an LED outputting UVC light in a band centered somewhere in the range of 200 to 280 nm), and/or light in the visible violet, blue or green wavelength ranges. In some embodiments, the light-delivery sheath assembly includes a motorized sheath-movement device configured to move one or more light-output ports within the patient (e.g., along the length of the urethra of the patient), in order that the time-and-intensity dose of light is sufficient to kill or inhibit undesirable microbes but without excessive damage to the patient's tissue. In some embodiments the kit includes a hemostatic agent. In some embodiments, the hemostatic agents include mechanical hemostats and/or sealants such as chitin and chitosan for surgical hemostasis but flowable solutions are not conventionally in development. The mechanical-hemostat technology has proven itself on the battlefield and in open, brisk bleeding control and cessation, and is used in some embodiments of the present invention.

In some embodiments, the catheters of the present invention are made of one or more of the following polymers: polyurethanes, polyamides, polyimides, fluoropolymers, polyolefins, polyvinyl chloride (PVC), and/or polyetheretherketone (PEEK).

In some embodiments, an interactive timed reminder device (such as described in European Patent EP 1210052 B1) is programmed to remind the patient and/or attending medical practitioner when the next of a series of temporally spaced-apart anti-microbial light treatment sessions is to be performed in order to reduce infections or the possibility thereof. The reminder communicated to the humans can help keep an effective schedule of anti-microbial light treatments.

In some embodiments, the apparatus is a kit that further includes an insertable and withdrawable LED-equipped sheath assembly having one or more LEDs that provide anti-microbial light in one or more wavelength bands, including, for example, ultraviolet (UV) irradiation in the C band, called UVC light, (e.g., from an LED outputting UVC light in a band centered somewhere in the range of 200 to 280 nm), and/or light in the visible violet, blue or green wavelength ranges. In some embodiments, the LED-equipped sheath assembly includes a motorized sheath-movement device configured to move one or more LEDs within the patient (e.g., along the length of the urethra of the patient), in order that the time-and-intensity dose of light is sufficient to kill or inhibit undesirable microbes but without excessive damage to the patient's tissue.

In some other embodiments, the apparatus further includes a light-propagation channel built into the catheter itself (such as one or more optical fibers) for the administration of anti-microbial ultraviolet light (and/or other wavelengths of light) along the catheter and/or at the distal end of the catheter to treat and/or prevent microbial (bacterial and/or fungal) infections.

In some embodiments, the apparatus is a kit that further includes an insertable and withdrawable image-acquisition sheath assembly having a light-propagation channel built into the sheath and/or LEDs at a distal end of the sheath, and a fiber-optic image-conduction channel or an imager at a distal end of the sheath, in order to obtain images along a length of the body lumen (e.g., in some embodiments, the urethra) of the patient.

BRIEF DESCRIPTION OF THE DRAWINGS

FIG. 1A is a side view, partially in cross section, of an unassembled system 101 having a specially modified Foley-type catheter 110, a medicament-delivery sheath 120, a light-delivery sheath 130, and a combined light-delivery-and-imaging sheath 140, according to some embodiments of the present invention.

FIG. 1B is a cross-sectional view of unassembled system 101 having Foley-type catheter 110, medicament-delivery sheath 120, light-delivery sheath 130, and combined light-delivery-and-imaging sheath 140, according to some embodiments of the present invention.

FIG. 1C1 is a side view, partially in cross section, of system 101' having Foley-type catheter 110 with medicament-delivery sheath 120 inserted therein, according to some embodiments of the present invention.

FIG. 1D1 is a cross-sectional view of system 101' having Foley-type catheter 110 with medicament-delivery sheath 120 inserted therein, at the plane of cross-section line 1D1 of FIG. 1C1, according to some embodiments of the present invention.

FIG. 1C2 is a side view of system 101" having Foley-type catheter 150 with medicament-delivery sheath 160 inserted therein, according to some embodiments of the present invention.

FIG. 1D2 is a cross-sectional view of system 101" having Foley-type catheter 150 with medicament-delivery sheath 160 inserted therein, at the plane of cross-section line 1D2 of FIG. 1C2, according to some embodiments of the present invention.

FIG. 1D3 is a cross-sectional view of system 101" having Foley-type catheter 150 with medicament-delivery sheath 160 inserted therein, at the plane of cross-section line 1D3 of FIG. 1C2, according to some embodiments of the present invention.

FIG. 1E1 is a side view, partially in cross section, of system 101" having Foley-type catheter 110 with light-delivery sheath 130 to be inserted therein, according to some embodiments of the present invention.

FIG. 1E2 is a side view of a light-delivery sheath insert 133, according to some embodiments of the present invention.

FIG. 1E3 is a side view of a light-delivery sheath insert 134, according to some embodiments of the present invention.

FIG. 1F1 is a side view, partially in cross section, of system 101'" having Foley-type catheter 150 with combined light-delivery-and-imaging sheath 140 to be inserted therein, according to some embodiments of the present invention.

FIG. 1F2 is a side view of a light-delivery sheath insert 135, according to some embodiments of the present invention.

FIG. 3A is a side view, partially in cross section, of an unassembled system 301 having a specially modified Foley-type catheter 310 and a medicament-delivery sheath 320, according to some embodiments of the present invention.

FIG. 3B1 is a cross-sectional view of unassembled system 301 having Foley-type catheter 310 and medicament-delivery sheath 320, according to some embodiments of the present invention.

FIG. 3B2 is a cross-sectional view of system 301' having Foley-type catheter 310 with medicament-delivery sheath 320 inserted therein, at line 3B2 of FIG. 3A, according to some embodiments of the present invention.

FIG. 3C is a side view, partially in cross section, of system 301' having Foley-type catheter 310 with medicament-delivery sheath 320 inserted therein, according to some embodiments of the present invention.

FIG. 5A is a side view, partially in cross section, of a system 501 having a specially modified Foley-type catheter 510 and a medicament-delivery coating 520 on the distal one-third portion 516, according to some embodiments of the present invention.

FIG. 5B is a cross-sectional view of system 501 having Foley-type catheter 510, according to some embodiments of the present invention.

FIG. 5C is a side view, partially in cross section, of system 501' having Foley-type catheter 510, according to some embodiments of the present invention.

FIG. 5D is a side view, partially in cross section, of a system 570 having a specially modified Foley-type catheter 571 and a medicament-delivery coating 520 on the distal one-third portion 516, according to some embodiments of the present invention.

FIG. 5E is a cross-sectional view of system 570 having Foley-type catheter 571 as viewed along section line 5E of FIG. 5D, according to some embodiments of the present invention.

FIG. 5F is a side view, partially in cross section, of system 570' having Foley-type catheter 571, according to some embodiments of the present invention.

FIG. 5G is a side view, partially in cross section, of a system 580 having a specially modified Foley-type catheter 581 and a medicament-delivery coating 520 on the distal one-third portion 516, according to some embodiments of the present invention.

FIG. 5H is a cross-sectional view of system 580 having Foley-type catheter 581 as viewed along section line 5H of FIG. 5G, according to some embodiments of the present invention.

FIG. 5i is a side view, partially in cross section, of system 580' having Foley-type catheter 581, according to some embodiments of the present invention.

FIG. 6A1 is a side view, partially in cross section, of a system 601 having a specially modified Foley-type catheter 610 and a medicament-delivery coating 620 on the distal one-third portion 616, according to some embodiments of the present invention.

FIG. 6A2 is a side view, partially in cross section, of a system 602 having a specially modified Foley-type catheter 610' and a medicament-delivery coating 620 on the distal one-third portion 616, along with an alignment insert 650, according to some embodiments of the present invention.

FIG. 6B1 is a cross-sectional view of system 601 having Foley-type catheter 610 as viewed along section line 6B1 of FIG. 6A1, according to some embodiments of the present invention.

FIG. 6B2 is a cross-sectional view of Foley-type catheter 610' of FIG. 6A2 as viewed along section line 6B2 of FIG. 6A2, according to some embodiments of the present invention.

FIG. 6B3 is a cross-sectional view of alignment insert 650 of FIG. 6A2 for aligning Foley-type catheter 610' as viewed along section line 6B3 of FIG. 6A2, according to some embodiments of the present invention.

FIG. 7A1 is a side view, partially in cross section, of a system 701 having a specially modified Foley-type catheter 710 without a medicament-delivery coating on the distal one-third portion, according to some embodiments of the present invention.

FIG. 7A2 is a side view, partially in cross section, of a system 702 having a specially modified Foley-type catheter 710' without a medicament-delivery coating on the distal one-third portion, along with an alignment insert 750, according to some embodiments of the present invention.

FIG. 7B1 is a cross-sectional view of system 701 having Foley-type catheter 710, according to some embodiments of the present invention.

FIG. 7B2 is a cross-sectional view of Foley-type catheter 710' of FIG. 7A2, according to some embodiments of the present invention.

FIG. 7B3 is a cross-sectional view of alignment insert 750 of FIG. 7A2 for aligning Foley-type catheter 710', according to some embodiments of the present invention.

FIG. 7C is a side view, partially in cross section, of system 701' having Foley-type catheter 710, according to some embodiments of the present invention.

FIG. 7D is a side view, partially in cross section, of system 701" having Foley-type catheter 710, according to some embodiments of the present invention.

DETAILED DESCRIPTION

Figure 1G:
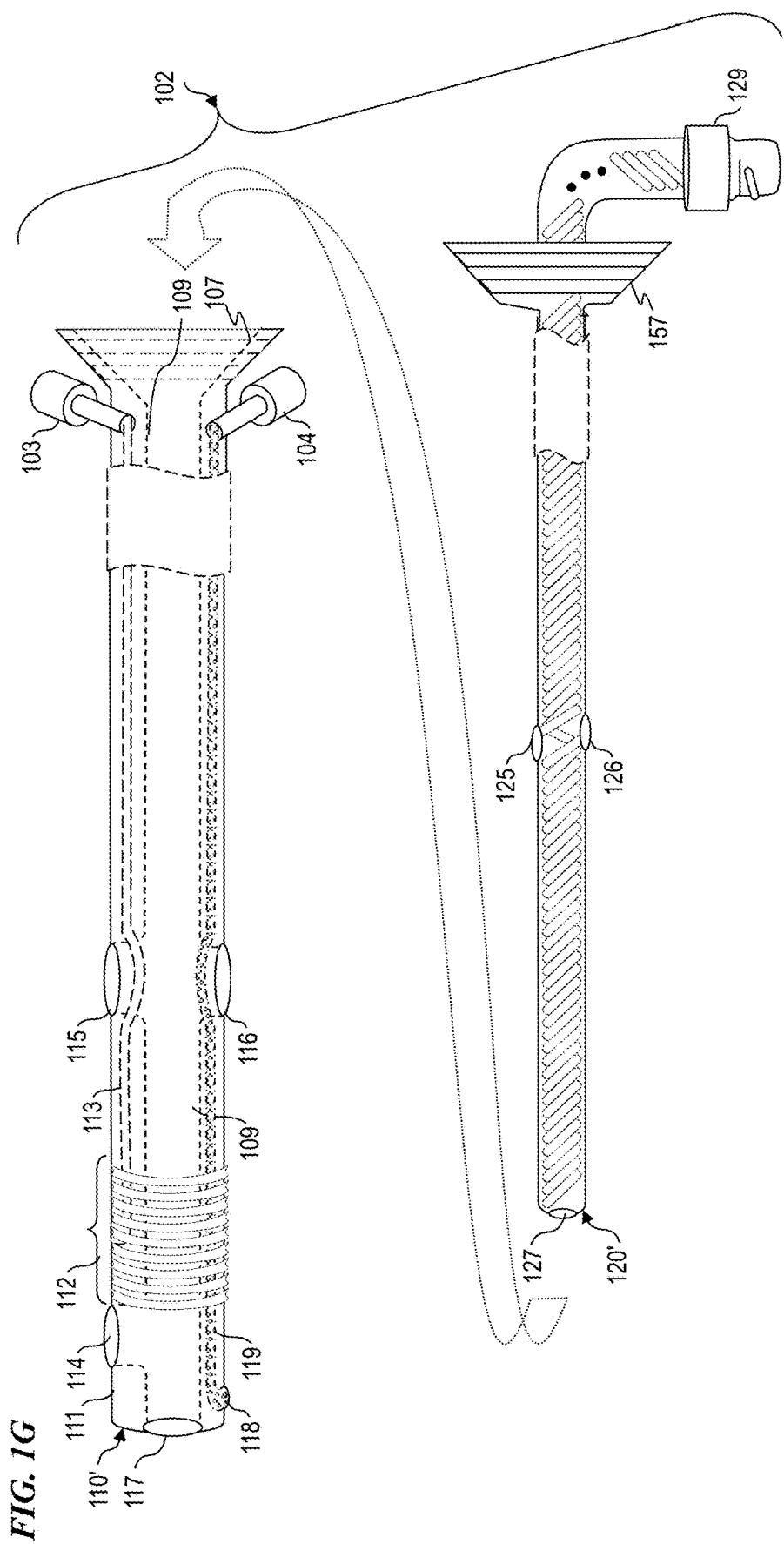
FIG. 1G is a side view, partially in cross section, of system 102 having Foley-type catheter 110' with medicament-delivery sheath 120' to be inserted therein, according to some embodiments of the present invention.

Although the following detailed description contains many specifics for the purpose of illustration, a person of ordinary skill in the art will appreciate that many variations and alterations to the following details are within the scope of the invention. Specific examples are used to illustrate particular embodiments; however, the invention described in the claims is not intended to be limited to only these examples, but rather includes the full scope of the attached claims. Accordingly, the following preferred embodiments of the invention are set forth without any loss of generality to, and without imposing limitations upon the claimed invention. Further, in the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention. The embodiments shown in the Figures and described here may include features that are not included in all specific embodiments. A particular embodiment may include only a subset of all of the features described, or a particular embodiment may include all of the features described.

The leading digit(s) of reference numbers appearing in the Figures generally corresponds to the Figure number in which that component is first introduced, such that the same reference number is used throughout to refer to an identical component which appears in multiple Figures. Signals and connections may be referred to by the same reference number or label, and the actual meaning will be clear from its use in the context of the description.

FIG. 1A is a side view of an unassembled system 101 having a specially modified Foley-type catheter 110, a medicament-delivery sheath 120, a light-delivery sheath 130, and a combined light-delivery-and-imaging sheath 140, according to some embodiments of the present invention. In some embodiments, catheter 110 has an inflatable and deflatable balloon section 112 configured to keep the catheter in place by inflating the balloon section 112 via lumen 113 with a fluid (such as saline, carbon dioxide gas or nitrogen gas) once the appropriate length of catheter 110 is inserted through the urethra of the patient so that the balloon section 112 is in the bladder of the patient.

In some embodiments, catheter 110 includes a central lumen 109 having an "outflow" distal-end port 117, typically used to drain a flush fluid that is injected through channel 119 and distal end port 118, and then drained from the bladder of the patient through central lumen 109. The "inflow" end port 118 connected to inflow lumen 119 is typically used to insert the flush fluid into the bladder of the patient, as is the case for a conventional Foley-type catheter. In some embodiments, central lumen 109 also includes a plurality of side ports 114, 115 and/or 116 (and/or other ports for embodiments (not shown) having other numbers of ports) used in the present invention to output and/or collect one or more medicaments at specific predetermined locations along the urethra and/or bladder. In some embodiments, one or more of the plurality of side ports, e.g., side ports 115 and/or 116, are spaced to be proximate to the prostate (see reference number 224 of FIG. 2A described below) in a male patient. Typically, a conventional Foley-type catheter is too pliable to be able to use to deposit a medicament, such as a hemostatic agent, at a specific location along the urethra or bladder since the medicament squirts out along the side of a syringe pushed against the conventional Foley-type catheter. In addition, a conventional Foley-type catheter is too flexible to be rotated by its end such that the side ports 114, 115 or 116 are "pointable" (rotationally and/or longitudinally movable) to align to a site of bleeding. Thus, in some embodiments, one or more of the sheaths 120, 130 and/or 140 are inserted temporarily and for enough time to perform a respective function associated with that particular sheath and then withdrawn in order to sequentially insert another sheath, perform its function, and then again withdraw that sheath when its function has been completed for a given time. For example, a light-delivery-and-imaging sheath 140 is used by the medical professional using system 101 to determine the location(s) needing treatment, a medicament-delivery sheath 120 is used to apply a hemostatic agent to stop bleeding, and then a light-delivery sheath 130 is used to deliver antimicrobial light to reduce or eliminate harmful microbes. In some embodiments, the sidewalls 111 of catheter 110 are made of a transparent material to facilitate imaging of the inside of the urethra using combined light-delivery-and-imaging sheath 140, to better allow the medical professional using system 101 to determine the location(s) needing treatment. In some embodiments, the proximal end of lumen 113 has a connector 103 used to connect to a source of the fluid (such as saline, carbon dioxide gas or nitrogen gas) used to inflate balloon 112. (As used herein, "proximal" refers to the end of the device closest to a medical professional during use of the device and "distal" refers to the end of the device furthest from the medical professional during use). In some embodiments, the proximal end of lumen 119 has a connector 104 used to connect to a source of the fluid (such as saline and/or a medicament) used to flush and/or treat infection of the bladder and/or urethra and/or ureters of the patient.

In other embodiments, catheter 110 has a reinforcing structure, such as a helical-wound nylon filament or tape embedded within, or on the outer and/or inner surface(s), to prevent radial expansion and/or to allow the catheter 110 to be rotated circumferentially within the urethra by rotation of the proximal end. In some embodiments, catheter 110 has a three-way reinforcing structure that is resistant to compression and obstruction. In some embodiments, catheter 110 is coated on its inner and/or outer surfaces to prevent sticking to the urethra and/or the insertable sheaths 120, 130 and/or 140. In some embodiments, catheter 110 is sterile and is provided in a package that is sealed until opened by an end user.

In some embodiments, medicament-delivery sheath 120 is coated with or otherwise includes an outer surface layer and/or inner surface layer that is/are hydrophilic. In some embodiments, medicament-delivery sheath 120 is sterile and is provided in a package that is sealed until opened by an end user. In some embodiments, medicament-delivery sheath 120 is designed to be a single-use device, but during any one treatment session a plurality of syringes 124 (see, e.g., FIG. 1C1) may be coupled to the single-use medicament-delivery sheath 120, depending on need.

In some other embodiments, catheter 110 has a structure that omits the balloon 112 and instead uses a Malecot structure with wings that buckle sideways inside the bladder to provide drainage and promote catheter retention, such as described in U.S. Pat. No. 6,527,737 titled "Indwelling urethra catheter," which is incorporated herein by reference.

According to the teachings of the present invention, medicament-delivery sheath 120 includes a flexible reinforcing structure 122 (such as a helical-wound non-magnetic metal wire (e.g., in some embodiments, titanium) selected to be compatible with magnetic-resonance imaging (MRI) systems, or such as described in U.S. Pat. No. 5,702,373 titled "Composite super-elastic alloy braid reinforced catheter," which is incorporated herein by reference) with a hydrophilic-coated outer material 121 configured to easily slide into the central lumen 109 of catheter 110. In some embodiments, one or more side ports (e.g. side ports 125 or 126) are pointable (via a rotation angle adjustment around the longitudinal axis and/or insertion-depth adjustment) to a site of bleeding, since the reinforcing structure 122 allows the medicament-delivery sheath 120 to be rotated from its proximal end while ports 125 and 126 extending outward from central longitudinal duct 152 also correspondingly rotate to a desired angle to be pointed toward a site of bleeding in the patient. In some embodiments, the distal end port 127 and/or one of the side ports 125 or 126 of medicament-delivery sheath 120 are omitted, in order that injected medicament is delivered out the remaining port(s). In some embodiments, system 101 includes a plurality of different versions of medicament-delivery sheath 120, each with different output ports, such that an appropriate medicament-delivery sheath 120 version can be chosen according to the treatment needed. In some embodiments, the cross-sectional profile of the outer surface of medicament-delivery sheath 120 (and, optionally, light-delivery sheath 130 and combined light-delivery-and-imaging sheath 140) and the cross-sectional profile of the inner surface of catheter 110 are correspondingly "keyed"—i.e., shaped in a non-cylindrical profile such that the catheter 110 will correspondingly rotate (around the longitudinal axis of catheter 110) within the urethra when the inserted medicament-delivery sheath 120 (and/or light-delivery sheath 130 and/or combined light-delivery-and-imaging sheath 140) is rotated, in order that the one or more output ports 114, 115 and/or 116 are aligned to a site of bleeding. In some embodiments, medicament-delivery sheath 120 includes a proximal input connector 129 (in some embodiments, a standard Luer-lock connection) configured to be connected to a standard syringe from which a medicament (such as a hemostatic agent and/or antibiotic) can be dispensed.

According to the teachings of the present invention, in some embodiments, light-delivery sheath 130 includes a flexible reinforcing structure 132 (such as a helical-wound non-magnetic metal wire (e.g., in some embodiments, titanium) selected to be compatible with magnetic-resonance imaging (MRI) systems, or such as described in U.S. Pat. No. 5,702,373 titled "Composite super-elastic alloy braid reinforced catheter," which is incorporated herein by reference) with a hydrophilic-coated outer material 131 configured to easily slide into the central lumen 109 of catheter 110. In some embodiments, light-delivery sheath 130 includes an end connection 139 configured to be removably attached to a light source (such as light-source system 138 as shown in FIG. 1E1 and described below). In some embodiments, an output light dispersion element 137 is provided at the distal end of light-delivery sheath 130 to output concentrated light circumferentially to one selected axial location along catheter 110 at a time. In some embodiments, delivery of 100 to 300 seconds of concentrated light is sufficient and appropriate to kill most pathogenic bacteria and fungi while minimizing damage to the patient's tissue, so the light-delivery sheath 130 is fully inserted into catheter 110 to initially deliver anti-microbial light to the bladder for an appropriate bladder-treatment time and intensity of UVC and/or other wavelengths of light, and then light-delivery sheath 130 is gradually withdrawn over a period of time such that each successive location along the entire length of the urethra is treated with an appropriate urethra-treatment time and intensity of UVC and/or other wavelength(s)s of light. Similar to the system described in U.S. Pat. No. 9,474,811 titled "Method of treating an eye infection using electromagnetic radiation in the UVC," which is incorporated herein by reference, in some embodiments of the present invention, a light-emitting diode producing UVC radiation at a wavelength of about 265 nm, at a power output of 5 mW, is directed on to a zone of genitourinary tissue about 12 mm$^2$ in area. In some embodiments, an optical aiming system indicates the zone of tissue to be irradiated. Irradiation for periods as brief as 1 second has been found effective in the system of U.S. Pat. No. 9,474,811, which equates to a dose of 4 mJ/cm$^2$ delivered to the tissue. In some embodiments, for treatment of the bladder, a gas such as air, carbon dioxide or nitrogen is inserted into the bladder such that the inner surface of the bladder is stretched out to expose the entire surface to the light treatment. In some embodiments, the intensity of the anti-microbial light is increased (and/or the terminal optical element 137 is modified to focus the light, rather than dispersing the light as is the case in the urethra) when the target area (e.g., when projecting light to the bladder wall) is much larger than when treating the urethra.

In other embodiments, the anti-microbial light is delivered to the bladder using a combined light-delivery-and-imaging sheath 140 that is configured to be manipulated to successively point to suitably small areas of the bladder wall so that the intensity per unit area is suitably high for a suitable treatment time and the entire bladder wall is scanned and treated with sufficient time and intensity of anti-microbial light to kill sufficient pathogens while minimizing tissue damage. In some embodiments, once the bladder is sufficiently treated, the light-delivery sheath 130 is automatically withdrawn at a predetermined rate under motorized control to deliver the appropriate urethra-treatment time and intensity of UVC and/or other wavelength(s)s of light along the entire length of the urethra. In some embodiments, combined light-delivery-and-imaging sheath 140 includes a tip that is manipulatable by a remote robotic system (such as described in U.S. Pat. No. 8,409,172 titled "Systems and methods for performing minimally invasive procedures," which is incorporated herein by reference) to point to different areas in the bladder to locate and/or treat specific areas of the bladder wall needing treatment using anti-microbial light.

According to the teachings of the present invention, in some embodiments, a combined light-delivery and imaging sheath 140 includes a flexible reinforcing structure 142 (such as a helical-wound non-magnetic metal wire (e.g., in some embodiments, titanium) selected to be compatible with magnetic-resonance imaging (MRI) systems, or such as described in U.S. Pat. No. 5,702,373 titled "Composite super-elastic alloy braid reinforced catheter," which is incorporated herein by reference) with a hydrophilic-coated outer material 141 configured to easily slide into the central lumen 109 of catheter 110. In some embodiments, combined light-delivery-and-imaging sheath 140 includes a distal end optics or imaging interface 147 configured to obtain image data from one main side direction. In some embodiments, combined light-delivery-and-imaging sheath 140 includes a proximal end connection 149 configured to be removably attached to a light source and imager system (such as light-source and imager system 148 as shown in FIG. 1F1 and described below) and distal imaging interface 147 (such as a lens or fiber-bundle termination), and catheter 110 is substantially transparent in order to obtain optical images of the insides of the bladder and/or urethra so the medical professional can locate the site of bleeding and/or infection. In some embodiments, catheter 110 is rotated using combined light-delivery-and-imaging sheath 140 such that the output ports 114, 115 and/or 116 are pointed to the location of needed treatment located by the imager. In some embodiments, combined light-delivery-and-imaging sheath 140 is used to also deliver UVC and/or other wavelength(s)s of light of appropriate intensity and treatment time to the bladder and/or along the entire length of the urethra. In some embodiments, the insertable sheaths 120, 130 and/or 140 are of suitable lengths and configuration to be inserted through the bladder into the ureters for treatment of one or both of the ureters.

According to the teachings of the present invention, in some other embodiments, combined light-delivery-and-imaging sheath 140 includes an MRI coil structure (such as described in U.S. Pat. No. 6,898,454 titled "Systems and methods for evaluating the urethra and the periurethral tissues," which is incorporated herein by reference). In some embodiments, combined light-delivery-and-imaging sheath 140 includes an end connection 149 configured to be removably attached to an MRI imaging system to obtain MR images of the urethra and the periurethral tissues. In some such embodiments, combined light-delivery-and-imaging sheath 140 omits structures (such as helical wire) that are or may be incompatible with MRI imaging.

According to the teachings of the present invention, in still other embodiments, combined light-delivery-and-imaging sheath 140 includes an ultrasonic transducer structure (such as described in U.S. Patent Application publication 20100137721 by Rose et al. titled "Transurethral Ultrasonic Imaging System," and/or U.S. Pat. No. 6,165,127 titled "Acoustic imaging catheter and the like," and/or U.S. Pat. No. 7,613,478 titled "Method and system for portability of clinical images using a high-quality display and portable device," which are each incorporated herein by reference). In some embodiments, combined light-delivery-and-imaging sheath 140 includes an end connection 149 configured to be removably attached to an ultrasonic imaging system to obtain ultrasonic images of the urethra and the periurethral tissues. In some such embodiments, combined light-delivery-and-imaging sheath 140 omits structures (such as helical wire) that are or may be incompatible with ultrasonic imaging.

In some embodiments, once the location needing treatment is located, combined light-delivery-and-imaging sheath 140 is removed from catheter 110 and medicament-delivery sheath 120 and/or light-delivery sheath 130 is/are successively inserted into catheter 110 to the determined location of needed treatment. In some embodiments, the keyed profile of catheter 110 and the respective sheaths 120, 130, and/or 140 allow rotational alignment (and the insertion depth) of catheter 110 to provide treatment delivery to the location needing treatment.

FIG. 1B is a cross-sectional view of unassembled system 101 along section line 1B of FIG. 1A (and enlarged in scale relative to the view in FIG. 1A) showing Foley-type catheter 110, medicament-delivery sheath 120, light-delivery sheath 130, and combined light-delivery-and-imaging sheath 140, according to some embodiments of the present invention. In some embodiments, the asymmetric shape of the outer surfaces 153 of medicament-delivery sheath 120, light-delivery sheath 130, and combined light-delivery-and-imaging sheath 140 are configured (e.g., "keyed" with corresponding cross-sectional shapes) to interface and align with the inner surface shape 151 of catheter 110 to allow rotational alignment of catheter 110 and the medicament-delivery sheath 120 and/or light-delivery sheath 130 and/or light-deliver-and-imaging sheath 140 and movement of the pair of devices 110 and 120 to an adjustable insertion depth to reach the location needing treatment. This also aligns the output ports 125 and/or 126 of medicament-delivery sheath 120 to the output ports 115 and/or 116 of catheter 110. In some embodiments, the cross-sectional shape of medicament-delivery sheath 120 has a flat external face 128 on one side and a rounded indented face 123 on the opposite side. In some embodiments, the corresponding flat internal face of central lumen 109 of catheter 110 provides extra space for lumen 119, and the corresponding protruding internal face of central lumen 109 provides extra space for lumen 113. In other embodiments, a symmetric non-cylindrical cross-sectional shape, such as a rectangle, triangle, pentagon or other suitable shape is used.

FIG. 1C1 is a side view of system 101' having a Foley-type catheter 110 with medicament-delivery sheath 120 inserted therein, according to some embodiments of the present invention. System 101' includes Foley-type catheter 110 and medicament-delivery sheath 120 of system 101 with the sheath 120 inserted inside catheter 110 such that the output ports 125 and/or 126 (see FIG. 1A) of medicament-delivery sheath 120 align to the output ports 115 and/or 116 of catheter 110. In some embodiments, the distal end port 127 and/or one of the side ports 125 or 126 of medicament-delivery sheath 120 are omitted, in order that injected medicament is delivered out the remaining port(s) to the location needing treatment. In some embodiments, a conventional syringe 124 is removably connected to the Luer-lock connection 129 of a selected medicament-delivery sheath 120 that is chosen such that the appropriate output port (of ports 127, 125 and/or 126) of medicament-delivery sheath 120 is proximal to the selected catheter port(s) 117, 114, 115 and/or 116 of catheter 110, next to the site of the patient needing treatment. In some embodiments, a removable cap-plug is provided on the Luer-lock connection 129 of medicament-delivery sheath 120. Section line 1D1 shows the location of the cross-sectional view of FIG. 1D1.

FIG. 1D1 is a cross-sectional view of system 101' along section line 1D1 of FIG. 1C1 (and enlarged in scale relative to the view in FIG. 1C1) having a Foley-type catheter 110 with medicament-delivery sheath 120 inserted therein, according to some embodiments of the present invention. FIG. 1C1 and FIG. 1D1 illustrate the alignment of output port 125 of medicament-delivery sheath 120 to output port 115 of catheter 110, and the alignment of output port 126 of medicament-delivery sheath 120 to output port 116 of catheter 110 that is facilitated by the keyed shape outer profile of medicament-delivery sheath 120 to the keyed shape inner profile of lumen 109 of catheter 110.

In some embodiments, the keyed shape outer profile of medicament-delivery sheath 120 and matching keyed shape inner profile of lumen 109 of catheter 110 facilitate the rotation of catheter 110 within the urethra such that a single set of output ports (e.g., port 115 of catheter 110 and port 125 of medicament-delivery sheath 120) are rotated and/or inserted to different depths together, to be located adjacent the site of bleeding before connection of syringe 124 to the Luer-lock connection 129 of medicament-delivery sheath 120 (i.e., little or no blood will exit Luer-lock connection 129 until port 115 is aligned to the site of bleeding, e.g., a site in the patient's urethra). Once that primary location of bleeding is determined, the syringe 124 with its load of hemostatic agent is then connected to Luer-lock connection 129 and the hemostatic agent is dispensed. In some embodiments, the cross-sectional shape of medicament-delivery sheath 120 has a flat external face 128 on one side and a rounded indented face 123 on the opposite side. In some embodiments, the corresponding flat internal face of central lumen 109 of catheter 110 provides extra space for lumen 119, and the corresponding protruding internal face of central lumen 109 provides extra space for lumen 113. In other embodiments, a symmetric non-cylindrical cross-sectional shape, such as a rectangle, triangle, pentagon or other suitable shape is used.

FIG. 1C2 is a side view of system 101" having Foley-type catheter 150 with medicament-delivery sheath 160 inserted therein, according to some embodiments of the present invention. Section line 1D2 shows the location of the cross-sectional view of FIG. 1D2. Section line 1D3 shows the location of the cross-sectional view of FIG. 1D3. Foley-type catheter 150 and sheath 160 differ from Foley-type catheter 110 and sheath 120 in that Foley-type catheter 150 has two side openings—a first opening 115 for outgoing medicament 99 and another opening 155 for returning excess medicament and/or blood or other fluids 99', and sheath 160 includes at least two interior channels—a first channel or duct 152 (see FIG. 1D2 and FIG. 1D3) for outgoing medicament 99 received from syringe 124 and a second channel 158 for returning excess medicament and/or blood or other fluids 99' through second channel 158 to connector 159 (which, in some embodiments, can be connected to a secondary syringe (not shown) for applying a lower pressure (e.g., vacuum) to assist in withdrawing fluid. This secondary syringe can be used by the medical practitioner to visually examine the returning excess medicament and/or blood or other fluids 99' to help determine that enough medicament is being applied to the location outside the catheter 150. In some embodiments, the relative sizes of channel 152 and channel 158 differ from those shown in FIG. 1C2, FIG. 1D2 and FIG. 1D3, e.g., being equal in size or with the outgoing second channel 158 being larger in diameter in order to more effectively remove clots that may occur in the leaking blood to which the hemostatic and/or anti-microbial medicament 99 is being applied.

FIG. 1D2 is a cross-sectional view of system 101" (enlarged in scale relative to the view in FIG. 1C2) having Foley-type catheter 150 with medicament-delivery sheath 160 inserted therein, at line 1D2 of FIG. 1C2, according to some embodiments of the present invention. In some embodiments, the cross-sectional shape of medicament-delivery sheath 160 has a flat external face 128 on one side and a rounded indented face 123 on the opposite side. In some embodiments, the corresponding flat internal face of central lumen 109 of catheter 150 provides extra space for lumen 119, and the corresponding protruding internal face of central lumen 109 provides extra space for lumen 113. In other embodiments, a symmetric non-cylindrical cross-sectional shape, such as a rectangle, triangle, pentagon or other suitable shape is used.

FIG. 1D3 is a cross-sectional view of system 101" (enlarged in scale relative to the view in FIG. 1C2) having Foley-type catheter 150 with medicament-delivery sheath 160 inserted therein, at line 1D3 of FIG. 1C2, according to some embodiments of the present invention. The other reference numbers in FIG. 1D2 and FIG. 1D3 are as described above.

FIG. 1E1 is a side view of system 101" having a Foley-type catheter 110 with light-delivery sheath 130 to be inserted therein, according to some embodiments of the present invention. In some embodiments, light-delivery sheath 130 is selectively connectable to motorized withdrawal and light-dose controller 138 via connector 139. In some embodiments, motorized withdrawal and light-dose controller 138 is programmable to automatically control the intensity of the anti-microbial light and the longitudinal position of the distal output light-dispersion element 137 so as to deliver the appropriate intensity and duration of treatment for each portion of the patient's tissue in the bladder 88 and along the length of urethra 89. In some embodiments, the medical professional will manually insert the light-delivery sheath 130 into catheter 110 and optionally set the treatment parameters into motorized withdrawal and light-dose controller 138, which then automatically controls the light intensity and the withdrawal positioning of light-delivery sheath 130 from catheter 110 over time, such that the bladder 88 and entire length of the urethra 89 are appropriately treated with anti-microbial light of the appropriate duration and intensity. In some embodiments, the LEDs in motorized withdrawal and light-dose controller 138 emit anti-microbial light in a wavelength range of about 260 nm to about 300 nm. In some embodiments, the wavelength of the anti-microbial light is centered at about 265 nm, while in other embodiments, the anti-microbial light is centered at about 275 nm or about 285 nm. In some embodiments, a plurality of LEDs is provided, wherein the individual LEDs or set of LEDs of the plurality of LEDs each provide different wavelengths and are individually activatable so as to provide a selectable set of one or more wavelengths suitable to kill a particular pathogenic microbe. In some embodiments, different wavelengths are driven to different intensity levels to kill a particular pathogenic microbe while minimizing damage to the patient's tissue. In some embodiments, the LED drivers in motorized withdrawal and light-dose controller 138 are controlled to provide the individual LEDs or sets of LEDs with the appropriate current to achieve the desired intensities.

FIG. 1E2 is a side view of a light-delivery sheath insert 133, according to some embodiments of the present invention. In some embodiments, light-delivery sheath insert 133, at its proximal end, includes a ball-shaped input end 144 suited to receive light, at a larger range of angles θ than flat-ended light waveguides, from LEDs in motorized withdrawal and light-dose controller 138. In some embodiments, light-delivery sheath insert 133 includes a helical scribed feature 146' configured to emit light across a length of the distal end of waveguide 143 to treat tissue on all sides of the distal end of waveguide 143.

FIG. 1E3 is a side view of a light-delivery sheath insert 134, according to some embodiments of the present invention. In some embodiments, light-delivery sheath insert 134, at its proximal end, includes a tapered input end 145 suited to receive light, at a larger range of angles θ than non-tapered flat-ended light waveguides, from LEDs in motorized withdrawal and light-dose controller 138. In some embodiments, light-delivery sheath insert 134 includes an angled facet 147 at its distal end configured to emit light sideways at an angle centered on propagation axis β at an exit cone having characteristic cone angle θ' from distal end of waveguide 143 to treat tissue on a particular side of the distal end of waveguide 143 (in some embodiments, light-delivery sheath insert 134 is rotatable to treat all sides of the surrounding tissue).

FIG. 1F1 is a side view of system 101'" having Foley-type catheter 150 with a combined light-delivery-and-imaging sheath 140 to be inserted therein, according to some embodiments of the present invention. In some embodiments, combined light-delivery and imaging sheath 140 is substantially similar to light-delivery sheath 130, but with the addition of distal-end imaging optics 147 and light-source and imaging system 148. As mentioned above, in some embodiments combined light-delivery-and-imaging sheath 140 includes a tip that is manipulatable by a remote robotic system (such as described in U.S. Pat. No. 8,409,172 titled "Systems and methods for performing minimally invasive procedures," which is incorporated herein by reference) to point to different areas in the bladder and/or urethra to locate and/or treat specific areas of the bladder wall needing treatment using anti-microbial light. In some embodiments, the display of light-source and imaging system 148 provides a real-time video image of the tissue area pointed at by distal end optics or imaging interface 147, in order that the medical professional doing the procedure can identify and/or treat the particular area of bladder 88 or urethra 89 needing treatment. In some embodiments, the distal optics 147 provide microscopic images of cells in the walls of the patient's urethra, bladder and/or ureters. In some embodiments, imaging system 148 of the present invention further includes a memory to save images obtained during the treatment and/or a machine-vision image processor used to perform a real-time pathology analysis of cells imaged (microscopically) during the treatment (such as described in U.S. Pat. No. 10,304,188 titled "Apparatus and method for automated cell analysis," which is incorporated herein by reference). In some embodiments, imaging system 148 of the present invention further includes a wired or wireless communications system that communicates image data to a separate computer such as a desktop personal computer in the local vicinity of the medical procedure being performed or to a computer server at remote location via the internet, wherein the local personal computer or remote server performs the image analysis (such as described in U.S. Pat. No. 10,304,188) and communicates back an enhanced image and/or pathology report for consideration by the attending physician.

In other embodiments (not shown), a sheath similar to light-delivery-and-imaging sheath 140 is provided to perform laser-light ablation and/or cauterization (e.g., in some embodiments, to control bleeding) to tissue of the walls of the patient's urethra, bladder and/or ureters. In some embodiments, light-source and imaging system 148 includes a laser-light-source system such as described in U.S. Pat. No. 8,784,461 titled "Method and apparatus for optical stimulation of nerves and other animal tissue," which is incorporated herein by reference, provides laser-light sources to provide nerve-stimulation functions to assist the surgeon in identifying nerve tissue to help avoid unnecessary damage to nerves of the genitourinary tract. In some embodiments, such a laser-light-source system provides high-power laser light for ablation and/or cauterization functions to remove tissue (such as, for example, malignant tissue of the prostate) and/or to stop bleeding.

In yet other embodiments (not shown), an electrical ablation-tipped sheath to insert into catheter 150 is provided (such as described in U.S. Pat. No. 10,022,183 titled "Temperature-responsive irrigated ablation/cauterization electrode with reduced coolant flow and related methods for making and using," which is incorporated herein by reference), which provides an electrical cauterization function to stop bleeding (e.g., at a site of bleeding identified using combined light-delivery-and-imaging sheath 140 of system 101''' shown in FIG. 1F1) and/or ablation function to remove unhealthy tissue. In some embodiments, the electrical ablation-tipped sheath injects a controlled amount of fluid during the ablation/cauterization procedures to control tip temperatures.

FIG. 1F2 is a side view of a light-delivery sheath insert 135, according to some embodiments of the present invention. In some embodiments, light-delivery sheath insert 135, at its proximal end, includes a ball-shaped input end 144 suited to receive light, at a larger range of angles θ than flat-ended light waveguides, from lasers in motorized withdrawal and light-dose controller 148. In some embodiments, light-delivery sheath insert 135 includes an angled facet 147 at its distal end configured to emit light sideways at a right angle from near the distal end of waveguide 143 to treat tissue on a particular side of the distal end of waveguide 143 (in some embodiments, light-delivery sheath insert 135 is rotatable to treat all sides of the surrounding tissue). In some embodiments, a transparent end portion 146 covers the end facet 147 to maintain total internal reflection at the facet 147 and to allow reflected light to exit sideways.

FIG. 1G is a side view of an alternative system 102 having Foley-type catheter 110' with medicament-delivery sheath 120' to be inserted therein, according to some embodiments of the present invention. In some embodiments, the proximal end of central lumen 109 ends in a conical ridged receiver 107 that receives conical stop 157 of medicament-delivery sheath 120', in order to provide a definite indication that medicament-delivery sheath 120' is fully inserted to the appropriate depth into catheter 110'. Other aspects of catheter 110' are the same as for catheter 110 of FIG. 1A-1F. Other aspects of medicament-delivery sheath 120' are the same as for medicament-delivery sheath 120 of FIG. 1A-1D. In some other embodiments, receiver 107 of catheter 110' and stop 157 of sheath 120' have other shapes and cross-sectional profiles, in order to better facilitate rotation of catheter 110' within the patient's urethra to correspond to the rotation of medicament-delivery sheath 120' to align to a treatment site in the patient's urethra.

Figure 2A:
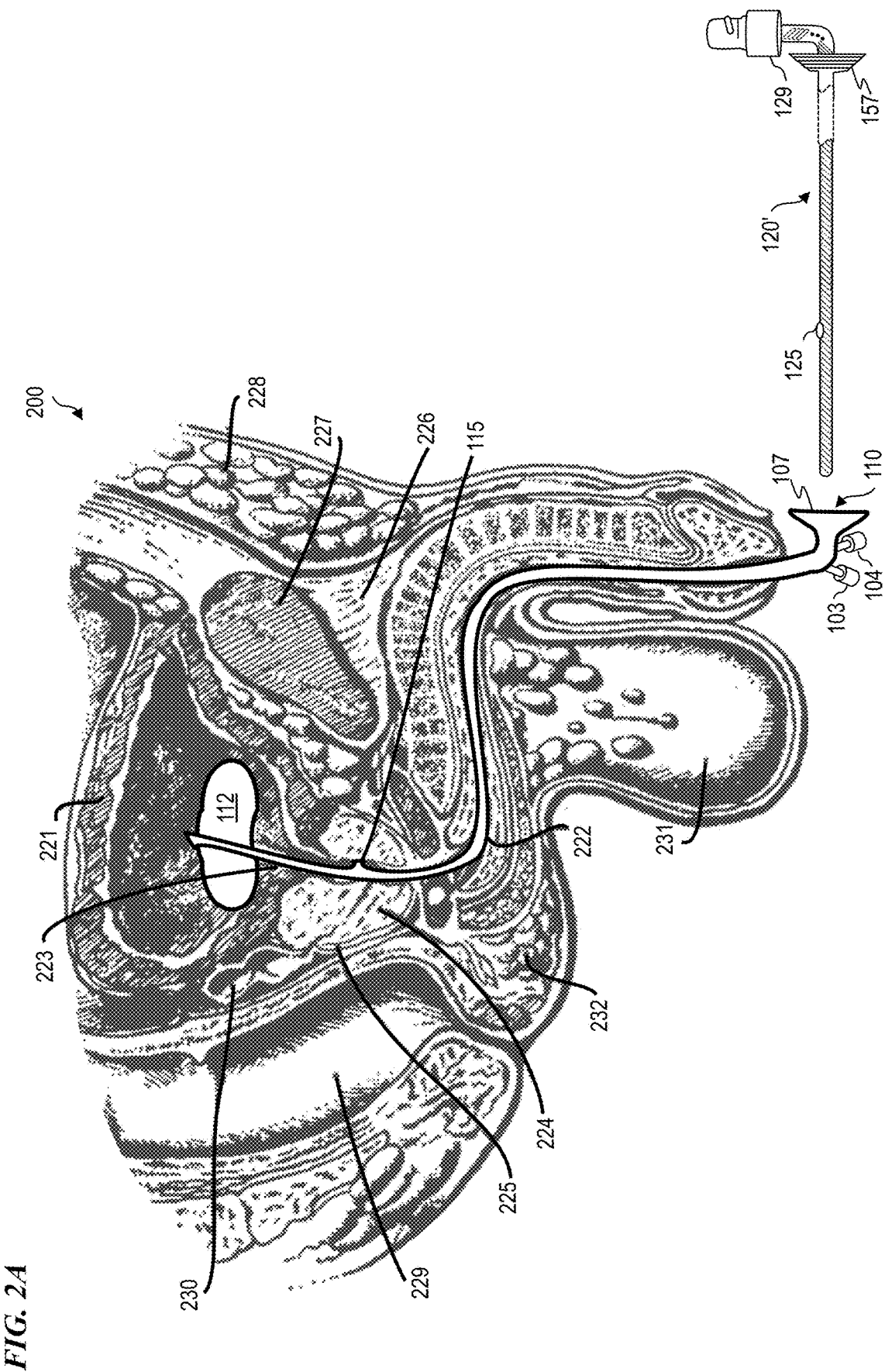
FIG. 2A is a cross-sectional view of the male pelvic region adapted from U.S. Pat. No. 2,799,273, schematically showing one possible placement of one embodiment of the present invention, according to some embodiments.

FIG. 2A is a hemisectional view of the male pelvic region 200 (adapted from U.S. Pat. No. 2,799,273 titled "HAEMOSTATIC CATHETER," which is incorporated herein by reference). The male pelvic region 200 includes a bladder 221, a urethra 222, and a vesical neck 223, which provides the muscular control between bladder 221 and the urethra 222. The prostate gland 224 is of generally conical shape and surrounds the urethra 222 just below the vesical neck 223. Prostate gland 224 is generally enclosed in a bed or sheath 225 that includes the peri-prostatic tissues. In front of this area are the suspensory ligament 226, a symphysis 227 and Camper's fascia 228. To the rear is the rectum 229 and the seminal vesicle 230. Below the area of prostate gland 224 are various glands and ducts, the scrotal septum 231, and the perineum 232. Referring to FIG. 2A, catheter 110 has been inserted through the urethra 222 and distal-end balloon 112 has been inflated to help keep catheter 110 in place with a single side port 115 located in the region of the prostate gland 224, and sheath 120' is about to be inserted into catheter 110.

Figure 2B:
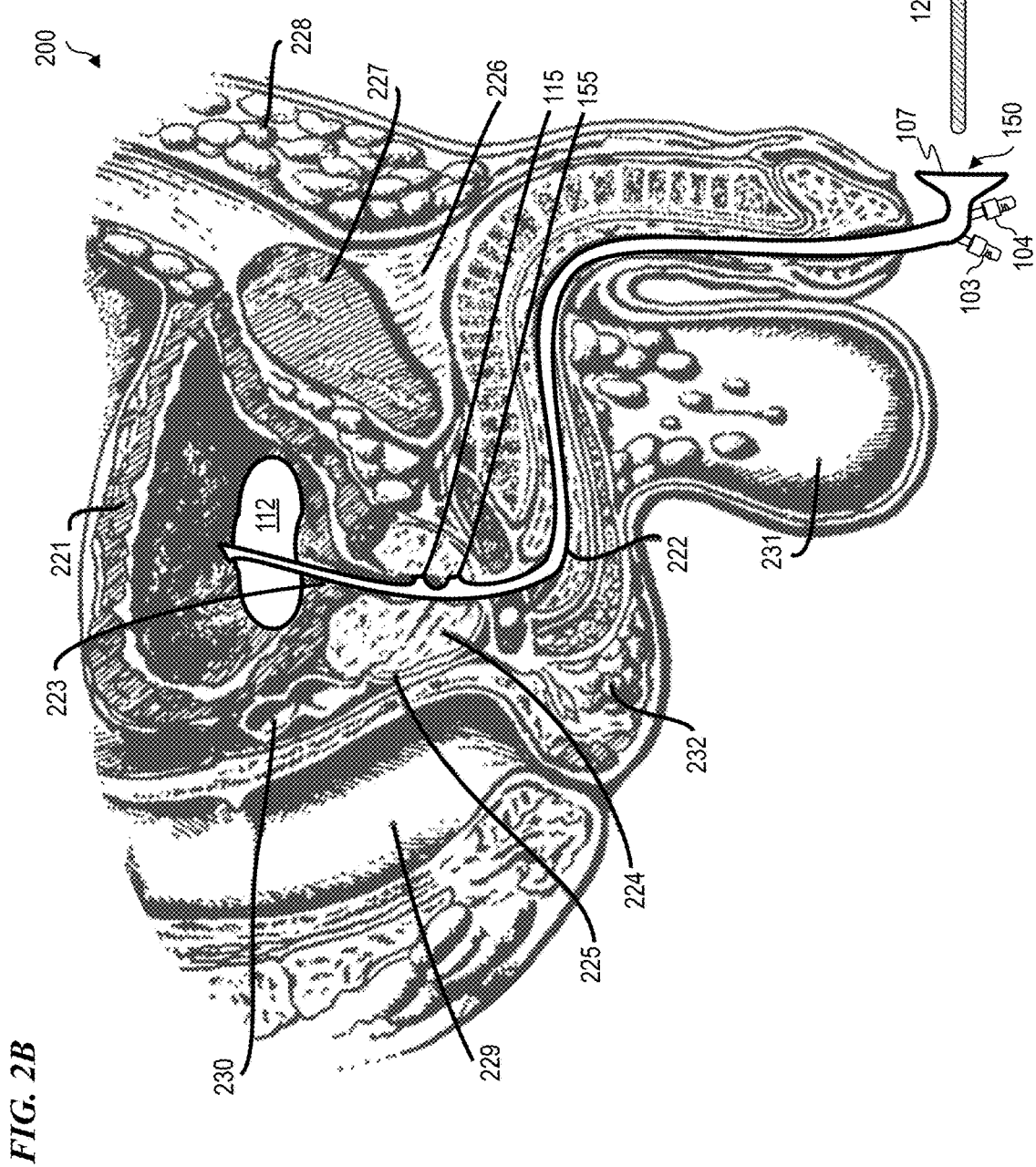
FIG. 2B is a cross-sectional view of the male pelvic region adapted from U.S. Pat. No. 2,799,273, schematically showing one possible placement of another embodiment of the present invention, according to some embodiments.

FIG. 2B is a hemisectional view of the male pelvic region adapted from U.S. Pat. No. 2,799,273, schematically showing one possible placement of the present invention, according to some embodiments. Referring to FIG. 2B, catheter 150 has been inserted through the urethra 222 and distal-end balloon 112 has been inflated to help keep catheter 150 in place with two side ports (catheter 150 output ports 115 and 155 aligning with sheath 160 output ports 125 and 156, respectively) located in the region of the prostate gland 224, and sheath 160 is about to be inserted into catheter 150.

FIG. 3A is a side view of an unassembled system 301 having a specially modified Foley-type catheter 310 and a medicament-delivery sheath 320, according to some embodiments of the present invention. In some embodiments, catheter 310 has an inflatable and deflatable balloon section 312 configured to keep the catheter in place by inflating the balloon section 312 via lumen 313 with a fluid (such as saline, carbon dioxide gas or nitrogen gas) once the appropriate length of catheter 310 is inserted through the urethra of the patient so that the balloon section 312 is in the bladder of the patient. In some embodiments, catheter 310 includes a central lumen 309 having an "outflow" distal-end port 317, typically used to drain a flush fluid that is injected through channel 319 and distal end port 318, and then drained from the bladder of the patient through central lumen 309. The "inflow" end port 318 connected to inflow lumen 319 and input port 304 is typically used to insert the flush fluid into the bladder of the patient, as is the case for a conventional Foley-type catheter. In some embodiments, central lumen 309 also includes one or more side ports 314, 315 and/or 316 (and/or other ports for embodiments (not shown) having other numbers of ports) used in the present invention to output one or more medicaments (or cleansing saline) and/or collect one or more medicaments, or bodily fluids, clots or debrided tissue at specific predetermined locations along the urethra and/or bladder and/or ureters. According to some embodiments, side ports 315 and 316 line up with ports 325 and 326, respectively, in sheath 320 when sheath 320 is inserted into central lumen 309. In some embodiments, one or more of the plurality of side ports, e.g., side ports 315 and/or 316, are spaced to be proximate to the prostate (see reference number 224 of FIG. 2A described above) in a male patient.

Typically, a conventional Foley-type catheter is too pliable to be able to use to deposit a medicament, such as a hemostatic agent, at a specific location along the urethra or bladder since the medicament squirts out along the side of the catheter or a syringe pushed against the conventional floppy Foley-type catheter. In addition, a conventional Foley-type catheter is typically too flexible to be rotated around its longitudinal axis by its end such that the side ports 314, 315 or 316 are pointable to align to a site of needed treatment. In some embodiments, the cross-sectional shape of medicament-delivery sheath 320 has a flat external face 328 on one side and a rounded indented face 323 on the opposite side. Thus, in some embodiments, one or more of the sheaths 320 (or sheaths 130 and/or 140 describe above) are used in a sequence to diagnose and/or treat a medical condition inside the patient's genitourinary tract. In some embodiments, the asymmetric shape of the outer surfaces 353 of medicament-delivery sheath 320 is configured (e.g., "keyed" with corresponding cross-sectional shapes) to interface and align with the inner surface shape 351 of catheter 310. In some embodiments, the flexible body portion of the medicament-delivery sheath 320 includes a first longitudinal (medicament injection) duct 352 that extends through the body portion of the medicament-delivery sheath from a proximal-end opening to, and in fluid communication with, a first intermediate side opening 325 and/or 326 between the proximal end at connector 329 and the distal end 327 of the medicament-delivery sheath 320. According to some embodiments, medicament-delivery sheath 320 includes a flexible reinforcing structure 322 (such as a helical-wound non-magnetic metal wire (e.g., in some embodiments, titanium) selected to be compatible with magnetic-resonance imaging (MRI) systems, or such as described in U.S. Pat. No. 5,702,373 titled "Composite super-elastic alloy braid reinforced catheter," which is incorporated herein by reference) with a hydrophilic-coated outer material 321 configured to easily slide into the central lumen 309 of catheter 310.

In some embodiments, the sidewalls 311 of catheter 310 are made of a transparent material to facilitate imaging of the inside of the urethra using combined light-delivery-and-imaging sheath 140, (not shown, but as shown in FIG. 1A) to better allow the medical professional using system 301 to determine the location(s) needing treatment. In some embodiments, the proximal end of lumen 313 has a connector 303 used to connect to a source of the fluid (such as saline, carbon dioxide gas or nitrogen gas) used to inflate balloon 312. In some embodiments, the proximal end of lumen 319 has a connector 304 used to connect to a source of the fluid (such as saline and/or a medicament) used to flush and/or treat infection of the bladder and/or urethra and/or ureters of the patient. In some embodiments, the proximal end of lumen 309 has a connector/interface (not shown, but such as shown in FIG. 1G) used to provide a depth and/or orientation guide for sheath 320.

FIG. 3B1 is a cross-sectional view of unassembled system 301 having Foley-type catheter 310 and medicament-delivery sheath 320 at line 3B1 of FIG. 3A, according to some embodiments of the present invention.

FIG. 3B2 is a cross-sectional view of system 301' having Foley-type catheter 310 with medicament-delivery sheath 320 inserted therein, at line 3B2 of FIG. 3A and line 3B2 of FIG. 3C, according to some embodiments of the present invention.

FIG. 3C is a side view of system 301' having Foley-type catheter 310 with medicament-delivery sheath 320 inserted therein, according to some embodiments of the present invention.

Figure 4A:
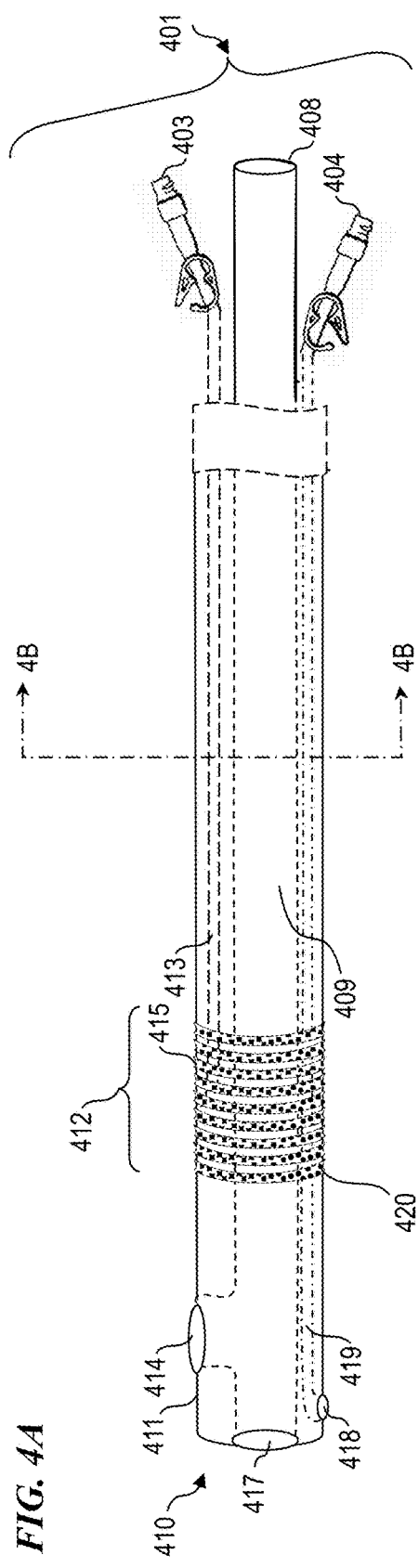
FIG. 4A is a side view, partially in cross section, of a system 401 having a specially modified Foley-type catheter 410 and a medicament-delivery coating 420 on the balloon portion 412, according to some embodiments of the present invention.

FIG. 4A is a side view, partially in cross section, of a system 401 having a specially modified Foley-type catheter 410 and a medicament-delivery coating 420 on the balloon portion 412, according to some embodiments of the present invention. In some embodiments, catheter 410 has side walls 411 made of a transparent material. According to some embodiments, catheter 410 has an inflatable and deflatable balloon section 412 configured to keep the catheter in place by inflating the balloon section 412 via lumen 413 and input port 403 with a fluid (such as saline, carbon dioxide gas or nitrogen gas) once the appropriate length of catheter 410 is inserted through the urethra of the patient so that the balloon section 412 is at the point of bleeding of the patient. The outer surface of balloon section 412 is coated with a medicament 415, such as a hemostatic agent, that is activated by the expansion of the balloon in the urethra or bladder. Thus, system 401 avoids the need for a medicament injection sheath, since the medicament 415 is on the balloon section 412. In some embodiments, catheter 410 includes a central lumen 409 having an "outflow" distal-end port 417, typically used to drain a flush fluid that is injected through channel 419 and distal end port 418, and then drained from the bladder of the patient through central lumen 409. The "inflow" end port 418 connected to inflow lumen 419 and input port 404 is typically used to insert the flush fluid into the bladder of the patient, as is the case for a conventional Foley-type catheter. In some embodiments, central lumen 409 also includes one or more side ports 414 (and/or other ports for embodiments (not shown) having other numbers of ports) used in the present invention to output one or more other medicaments (or cleansing saline) and/or collect one or more medicaments, or bodily fluids, clots or debrided tissue at specific predetermined locations along the urethra and/or bladder and/or ureters. In some embodiments, the proximal end of lumen 413 has a connector 403 used to connect to a source of the fluid (such as saline, carbon dioxide gas or nitrogen gas) used to inflate balloon 412. In some embodiments, the proximal end of lumen 419 has a connector 404 used to connect to a source of the fluid (such as saline and/or a medicament) used to flush and/or treat infection of the bladder and/or urethra and/or ureters of the patient. In some embodiments, the proximal end of lumen 409 has an open end 408 for drainage of fluids.

Figure 4B:
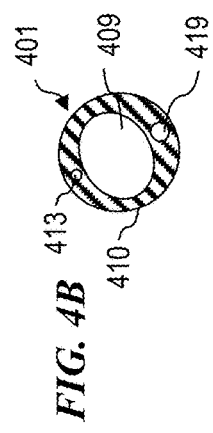
FIG. 4B is a cross-sectional view of system 401 having Foley-type catheter 410, according to some embodiments of the present invention.

FIG. 4B is a cross-sectional view of system 401 having Foley-type catheter 410, according to some embodiments of the present invention.

Figure 4C:
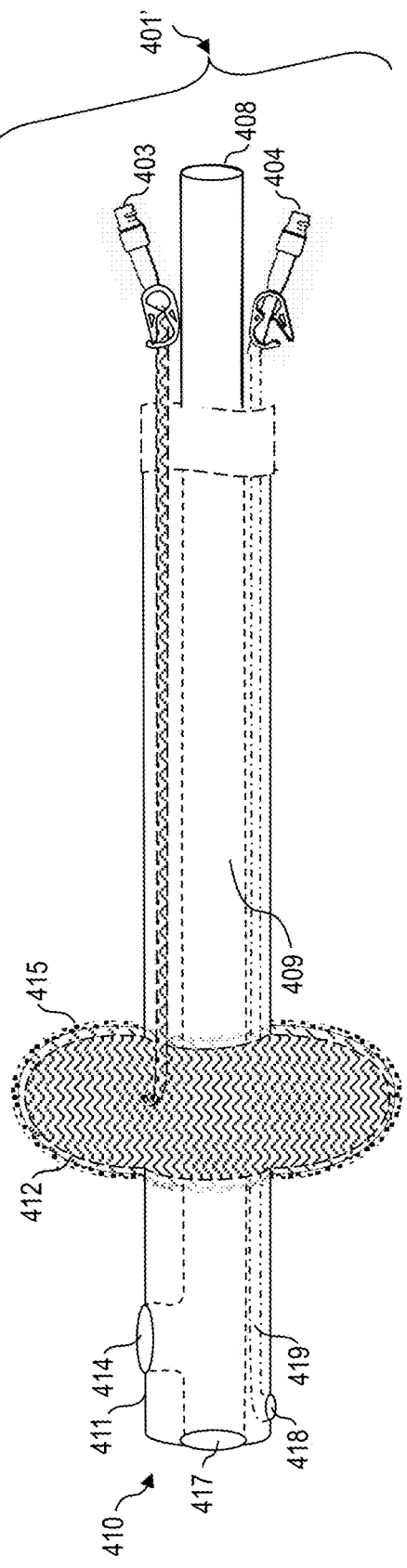
FIG. 4C is a side view, partially in cross section, of system 401' having Foley-type catheter 410, according to some embodiments of the present invention.

FIG. 4C is a side view, partially in cross section, of system 401' having Foley-type catheter 410, according to some embodiments of the present invention. In FIG. 4C, the balloon section 412 has been inflated, which releases/activates the medicament 415, such as a hemostatic agent.

FIG. 5A is a side view, partially in cross section, of a system 501 having a specially modified Foley-type catheter 510 and a medicament-delivery coating 520 on the distal one-third portion 516, according to some embodiments of the present invention. In other embodiments, the medicament-delivery coating 520 is instead or additionally on other portions (other than portion 516) of catheter 510. In some embodiments, catheter 510 has side walls 511 made of a transparent material. According to some embodiments, catheter 510 has an inflatable and deflatable balloon section 512 configured to keep the catheter in place by inflating the balloon section 512 via lumen 513 and input port 503 with a fluid (such as saline, carbon dioxide gas or nitrogen gas) once the appropriate length of catheter 510 is inserted through the urethra of the patient so that the balloon section 512 is at the point of bleeding of the patient. The outer surface of the distal end portion is coated with a medicament-delivery coating 520, such as a hemostatic agent, that is activated by contact with liquid, such as blood or urine, in the urethra or bladder. Thus, system 501 avoids the need for a medicament injection sheath, since the medicament-delivery coating 520 is on the entire distal end (or other suitable portion) of catheter 510.

In some embodiments (not shown here), catheter 510 has medicament-delivery coating 520 on the surface of balloon portion 512 but not on the portion of catheter 510 between the balloon portion 512 and the distal end of distal-end port 517 (in some embodiments, this is useful for inflating the balloon portion at the point of bleeding along the urethra, such as the prostate, allowing the application of pressure against the tissue where the bleeding is occurring). In some other embodiments (not shown here), catheter 510 has medicament-delivery coating 520 on the surface of balloon portion 512 and on a length (in some embodiments, a length of about 5 cm, about 10 cm, about 15 cm, about 20 cm, about 25 cm, about 30 cm, or an entire length) of the surface of catheter 510 between balloon portion 512 and the proximal end of catheter 510, but not on the portion of catheter 510 between the balloon portion 512 and the distal end of distal-end port 517. In still other embodiments (not shown here), catheter 510 has no medicament-delivery coating 520 on the surface of balloon portion 512 nor on the portion of catheter 510 between the balloon portion 512 and the distal end of distal-end port 517, but does have medicament-delivery coating 520 on a length (in some embodiments, a length of about 5 cm, about 10 cm, about 15 cm, about 20 cm, about 25 cm, about 30 cm, or an entire length) of the surface of catheter 510 between balloon portion 512 and the proximal end of catheter 510.

In some embodiments, the release of medicament-delivery coating 520 from catheter 510 relies on liquid (e.g., blood and/or urine) already in the patient's urethra and/or bladder. In some embodiments, the release of medicament-delivery coating 520 from catheter 510 additionally or alternatively relies on liquid (e.g., saline, additional medicament, or other suitable liquid) that is pushed into the patient's urethra and/or bladder via input-port connector 504 lumen 519 and port 518.

In some embodiments, catheter 510 includes a central lumen 509 having an "outflow" distal-end port 517, typically used to drain a flush fluid that is injected through channel 519 and distal end port 518, and then drained from the bladder of the patient through central lumen 509. The "inflow" end port 518 connected to inflow lumen 519 and input-port connector 504 is typically used to insert the flush fluid into the bladder of the patient, as is the case for a conventional Foley-type catheter. In some embodiments, this flush fluid is a liquid configured to activate and/or release the medicament in coating 520. In some embodiments, central lumen 509 also includes one or more side ports 514 (and/or other ports for embodiments (not shown) having other numbers of ports) used in the present invention to output one or more other (additional) medicaments (or cleansing saline) and/or collect one or more medicaments, or bodily fluids, clots or debrided tissue at specific predetermined locations along the urethra and/or bladder and/or ureters. In some embodiments, the proximal end of lumen 513 has a connector 503 used to connect to a source of the fluid (such as saline, carbon dioxide gas or nitrogen gas) used to inflate balloon 512. In some embodiments, the proximal end of lumen 519 has an input-port connector 504 used to connect to a source of the fluid (such as saline and/or a medicament) used to flush and/or treat infection of the bladder and/or urethra and/or ureters of the patient. In some embodiments, the proximal end of lumen 509 has an open end 508 for discharge of drained fluids.

FIG. 5B is a cross-sectional view of system 501 having Foley-type catheter 510 as viewed along section line 5B of FIG. 5A, according to some embodiments of the present invention.

FIG. 5C is a side view, partially in cross section, of system 501' having Foley-type catheter 510, according to some embodiments of the present invention. In FIG. 5C, the balloon section 512 has been inflated to hold the catheter 510 in place, and a liquid such as urine or blood or saline injected through port 518 has contacted the dried and/or cured (e.g., in some embodiments, cured to a solid form from a liquid form by ultraviolet light) medicament-delivery coating 520 (not labeled, but as shown in FIG. 5A) which releases/activates the activated medicament 515, such as a hemostatic agent, when contacted by a liquid that includes water (such as urine or blood).

FIG. 5D is a side view, partially in cross section, of a system 570 having a specially modified Foley-type catheter 571 and a medicament-delivery coating 520 on the distal one-third portion 516, according to some embodiments of the present invention. In some embodiments, catheters 571 of the present invention otherwise similar to catheter 510 include two or more balloon portions including distal-end balloon portion 512 and one or more additional balloon portions 572 that are coated with medicament-delivery coating 520, such that distal-end balloon portion 512 can be inflated in the bladder of the patient, the catheter 571 pulled outward relative to the patient such that distal-end balloon portion 512 is anchored at the proximal end of the bladder, then one or more of the one or more additional balloon portions 572 that are coated with medicament-delivery coating 520 are individually inflated (in some embodiments, independent of other such balloon portions 572 not shown here) via input port 574 and lumen 573 to release the medicament(s) by stretching the outer surface and medicament-delivery coating 520 and/or to also apply pressure at those locations along the urethra that are bleeding and/or that need infection-fighting medicament(s) at those specific locations.

FIG. 5E is a cross-sectional view of system 570 having Foley-type catheter 571 as viewed along section line 5E of FIG. 5D, according to some embodiments of the present invention.

FIG. 5F is a side view, partially in cross section, of system 570' having Foley-type catheter 571, according to some embodiments of the present invention. In FIG. 5F, the distal-end balloon section 512 has been inflated (generally in the bladder of the patient) to hold the catheter 571 in place, and a liquid such as urine or blood normally in the patient (or saline injected through port 518) has contacted the medicament-delivery coating 520 (not labeled, but as shown in FIG. 5D) which releases/activates the activated medicament 515, such as a hemostatic agent, when contacted by a liquid that includes water (such as urine or blood) or other suitable liquid. In some embodiments, the inflated portion 572 (and/or other additional inflatable balloon portions at other locations along catheter 571) applies pressure at the location(s) along the urethra that are bleeding and/or that need infection-fighting medicament(s) at those specific locations.

FIG. 5G is a side view, partially in cross section, of a system 580 having a specially modified Foley-type catheter 581 and a medicament-delivery coating 520 on the distal one-third portion 516, according to some embodiments of the present invention. In some embodiments catheters 581 of the present invention otherwise similar to catheter 510 include fiber-optic light conduit(s) 583 (not labeled, but as shown in FIG. 5i) that receive light through connector 584 and apply that light (having ultraviolet and/or other suitable wavelengths) via output end 582 (not labeled, but as shown in FIG. 5i) at those locations along the urethra that need infection-fighting light wavelength(s) at those specific locations. In some embodiments, the output end 582 is inside one of the balloon portions 512 and/or 572.

FIG. 5H is a cross-sectional view of system 580 having Foley-type catheter 581 as viewed along section line 5H of FIG. 5G, according to some embodiments of the present invention.

FIG. 5i is a side view, partially in cross section, of system 580' having Foley-type catheter 581, according to some embodiments of the present invention. In FIG. 5i, the distal-end balloon section 512 has been inflated (generally in the bladder of the patient) to hold the catheter 581 in place, and a liquid such as urine or blood normally in the patient (or saline injected through port 518) has contacted the medicament-delivery coating 520 (not labeled, but as shown in FIG. 5G) which releases/activates the activated medicament 515, such as a hemostatic agent, when contacted by a liquid that includes water (such as urine or blood) or other suitable liquid. In some embodiments, the secondary inflated portion 572 (and/or other additional inflatable balloon portions at other locations along catheter 581) applies pressure at the location(s) along the urethra that are bleeding and/or that need infection-fighting medicament(s) at those specific locations. In other embodiments, (not shown), the secondary balloon portions 572 are omitted but the light delivery features 582, 583, and 584 are retained to apply light inside the urethra and/or bladder of the patient. In some embodiments, the light activates or helps activate the release of the medicament 515 from medicament-delivery coating 520.

Figures 6C, 6D:
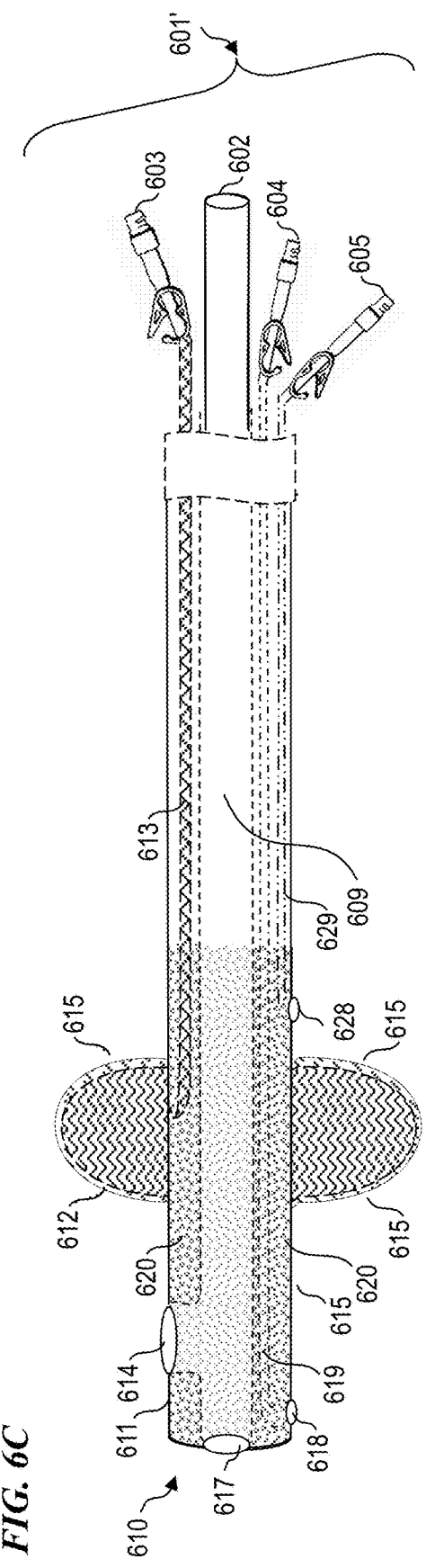
FIG. 6C is a side view, partially in cross section, of system 601' having Foley-type catheter 610, according to some embodiments of the present invention.
FIG. 6D is a side view, partially in cross section, of system 601" having Foley-type catheter 610, according to some embodiments of the present invention.

FIG. 6A1 is a side view, partially in cross section, of a system 601 having a specially modified Foley-type catheter 610 and a medicament-delivery coating 620 on the distal one-third portion 616, according to some embodiments of the present invention. In some embodiments, catheter 610 has side walls 611 made of a transparent material. According to some embodiments, catheter 610 has an inflatable and deflatable balloon section 612 configured to keep the catheter in place by inflating the balloon section 612 via lumen 613 and input port 603 with a fluid (such as saline, carbon dioxide gas or nitrogen gas) once the appropriate length of catheter 610 is inserted through the urethra of the patient so that the balloon section 612 is at the point of bleeding of the patient, or in the bladder of the patient. The outer surface of the distal end portion 616 is coated with a medicament-delivery coating 620, such as a hemostatic agent, that is activated by contact with liquid, such as blood or urine, already in the urethra or bladder, and/or by liquid (such as saline) that is injected through input port 605, lumen 629 and output port 628. This portion is defined as a coated end portion 616. According to some embodiments, coated end portion 616 begins proximal to output port 628. Thus, system 601 avoids the need for a medicament injection sheath, since the medicament-delivery coating 620 is on the entire distal end, and system 601 includes liquid-injection passageway (activation-fluid-input port 605—lumen 629—activation-fluid-output port 628 to allow a liquid to be injected to activate the medicament coating 620. In some embodiments, catheter 610 includes a central lumen 609 having an "outflow" distal-end port 617, typically used to drain a flush fluid from the bladder of the patient that is injected through channel 619 and distal end port 618, and then drained from the bladder of the patient through central lumen 609. The "inflow" end port 618 connected to inflow lumen 619 and input port 604 is typically used to insert the flush fluid into the bladder of the patient, as is the case for a conventional Foley-type catheter. In some embodiments, central lumen 609 also includes one or more side ports 614 (and/or other ports for embodiments (not shown) having other numbers of ports) used in the present invention to output one or more other medicaments (or cleansing saline or a liquid used to release and/or activate the medicament 615 (not labeled, but as shown in FIG. 6C) from coating 620) and/or collect one or more medicaments, or bodily fluids, clots or debrided tissue at specific predetermined locations along the urethra and/or bladder and/or ureters. In some embodiments, the proximal end of lumen 613 has a connector 603 used to connect to a source of the fluid (such as saline, carbon dioxide gas or nitrogen gas) used to inflate balloon 612. In some embodiments, the proximal end of lumen 619 has a connector 604 used to connect to a source of the fluid (such as saline and/or a medicament) used to flush and/or treat infection of the bladder and/or urethra and/or ureters of the patient. In some embodiments, the proximal end of lumen 609 has an open end 608 for discharge of drained fluids. In some embodiments, the proximal end of lumen 629 has a connector 605 used to connect to a source of the activation fluid (such as saline and/or a further medicament) used to activate medicament 615 from coating 620 and/or treat infection of the bladder and/or urethra and/or ureters of the patient.

FIG. 6A2 is a side view, partially in cross section, of a system 602 having a specially modified Foley-type catheter 610' and a medicament-delivery coating 620 on the distal one-third portion 616 (not labeled, but as shown in FIG. 6A1), along with an alignment insert 650, according to some embodiments of the present invention. According to some embodiments, the proximal end of lumen 609' has an open end 607 for discharge of drained fluids. In some embodiments, alignment insert 650 has a non-circular cross section and is insertable into lumen 609' (which has a corresponding non-circular cross section) to allow the urologist physician or other medical practitioner to rotate (twist around a longitudinal axis) the catheter 610' to better align exit ports 628, 618, and/or 614 to point in a desired orientation (such as pointing towards a bleeding site). Other aspects of Foley-type catheter 610' of FIG. 6A2 are substantially similar to Foley-type catheter 610 of FIG. 6A1.

FIG. 6B1 is a cross-sectional view (along section line 6B1 of FIG. 6A1) of system 601 of FIG. 6A1 having Foley-type catheter 610, according to some embodiments of the present invention.

FIG. 6B2 is a cross-sectional view (along section line 6B2 of FIG. 6A2) of Foley-type catheter 610' of FIG. 6A2, according to some embodiments of the present invention.

FIG. 6B3 is a cross-sectional view (along section line 6B3 of FIG. 6A2) of alignment insert 650 of FIG. 6A2 for aligning Foley-type catheter 610', according to some embodiments of the present invention. According to some embodiments, the shape of the outer surfaces 659 of alignment insert 650 is configured (e.g., "keyed" with corresponding cross-sectional shapes) to interface and align with the inner surface shape of lumen 609' of catheter 610'. In some embodiments, alignment insert 650 is inserted into lumen 609' of catheter 610' and twisted to align output port 628 and/or output ports 614 or 618 to desired orientations.

FIG. 6C is a side view, partially in cross section, of system 601' having Foley-type catheter 610, according to some embodiments of the present invention. In FIG. 6C, the balloon section 612 has been inflated to hold the catheter 610 in place, and a liquid such as urine or blood or saline injected through port 628 via lumen 629 and input port 605 (and/or port 618 via lumen 619 and input port 604) has contacted the dried and/or cured (e.g., in some embodiments, cured to a solid form from a liquid form by ultraviolet light) medicament-delivery coating 620 (not labeled, but as shown in FIG. 6A1) which releases/activates the activated medicament 615, such as a hemostatic agent, when contacted by a liquid that includes water (such as urine or blood).

FIG. 6D is a side view, partially in cross section, of system 601" having Foley-type catheter 610, according to some embodiments of the present invention. In FIG. 6D, the balloon section 612 has been inflated to hold the catheter 610 in place. And a liquid such as saline injected through port 628 (or port 618) has contacted the dried and/or cured (e.g., in some embodiments, cured to a solid form from a liquid form by ultraviolet light) medicament-delivery coating 620 (not labeled, but as shown in FIG. 6A1) which releases/activates the activated medicament 615, such as a hemostatic agent, when contacted by a liquid that includes water (such as urine or blood).

FIG. 7A1 is a side view, partially in cross section, of a system 701 having a specially modified Foley-type catheter 710 (similar to system 601 of FIG. 6A1 but without a medicament-delivery coating), according to some embodiments of the present invention. In some embodiments, catheter 710 has side walls 711 made of a transparent material. According to some embodiments, catheter 710 has an inflatable and deflatable balloon section 712 configured to keep the catheter 710 in place by inflating the balloon section 712 via lumen 713 and input port 703 with a fluid (such as saline, carbon dioxide gas or nitrogen gas) once the appropriate length of catheter 710 is inserted through the urethra of the patient so that the balloon section 712 is at the point of bleeding of the patient, or in the bladder of the patient. In some embodiments, catheter 710 includes a medicament-delivery passageway (including input port 705, lumen 729 and output port 728) used to deposit medicament at a location of bleeding and/or infection. Thus, system 701 avoids the need for a medicament injection sheath such as shown in FIG. 1A, since the medicament is delivered via a passageway and connector that are part of catheter 710. In some embodiments, catheter 710 includes a central lumen 709 having an "outflow" distal-end port 717, typically used to drain a flush fluid from the bladder of the patient that is injected through channel 719 and distal end port 718, and then drained from the bladder of the patient through central lumen 709. The "inflow" end port 718 connected to inflow lumen 719 and input port 704 is typically used to insert the flush fluid into the bladder of the patient, as is the case for a conventional Foley-type catheter, but in some embodiments, this lumen 719 can also be used to deposit medicament. In some embodiments, central lumen 709 also includes one or more side ports 714 (and/or other ports for embodiments (not shown) having other numbers of ports) used in the present invention to output one or more other medicaments (or cleansing saline) and/or collect one or more medicaments, or bodily fluids, clots or debrided tissue at specific predetermined locations along the urethra and/or bladder and/or ureters. In some embodiments, the proximal end of lumen 713 has a connector 703 used to connect to a source of the fluid (such as saline, carbon dioxide gas or nitrogen gas) used to inflate balloon 712. In some embodiments, the proximal end of lumen 719 has a connector 704 used to connect to a source of the fluid (such as saline and/or a medicament) used to flush and/or treat infection of the bladder and/or urethra and/or ureters of the patient. In some embodiments, the proximal end of lumen 709 has an open end 708 for discharge of drained fluids. In some embodiments, the proximal end of lumen 729 has a connector 705 used to connect to a source of the medicament 715 (See FIG. 7D) to treat infection of the bladder and/or urethra and/or ureters of the patient.

FIG. 7A2 is a side view, partially in cross section, of a system 702 having a specially modified Foley-type catheter 710', along with an alignment insert 750, according to some embodiments of the present invention. In some embodiments, alignment insert 750 has a non-circular cross section and is insertable into lumen 709' (which has a corresponding non-circular cross section) to allow the urologist physician or other medical practitioner to rotate (twist around a longitudinal axis) the catheter 710' to better align exit port 728 and/or other ports 714 and/or 718 to point in a desired orientation (such as pointing towards a bleeding site). Other aspects of Foley-type catheter 710' of FIG. 7A2 are substantially similar to Foley-type catheter 710 of FIG. 7A1.

FIG. 7B1 is a cross-sectional view (along section line 7B1 of FIG. 7A1) of system 701 of FIG. 7A1 having Foley-type catheter 710, according to some embodiments of the present invention.

FIG. 7B2 is a cross-sectional view (along section line 7B2 of FIG. 7A2) of Foley-type catheter 710' of FIG. 7A2, according to some embodiments of the present invention.

FIG. 7B3 is a cross-sectional view (along section line 7B3 of FIG. 7A2) of alignment insert 750 of FIG. 7A2 for aligning Foley-type catheter 710', according to some embodiments of the present invention. According to some embodiments, the shape of the outer surfaces 759 of alignment insert 750 is configured (e.g., "keyed" with corresponding cross-sectional shapes) to interface and align with the inner surface shape of lumen 709 of catheter 710. In some embodiments, alignment insert 750 is inserted into lumen 709' of catheter 710' and twisted to align output port 728 and/or output ports 714 or 718 to desired orientations.

FIG. 7C is a side view, partially in cross section, of system 701' having Foley-type catheter 710, according to some embodiments of the present invention. In FIG. 7C, the balloon section 712 has been inflated to hold the catheter 710 in place.

FIG. 7D is a side view, partially in cross section, of system 701" having Foley-type catheter 710, according to some embodiments of the present invention. In FIG. 7D, the balloon section 712 has been inflated to hold the catheter 710 in place, and a medicament 715 injected through output port 728, such as a hemostatic agent. In some embodiments, medicament can also be output via port 718.

In some embodiments, the present invention uses dip coating with UV curing with a step-by-step method for applying a hydrophilic coating (e.g., medicament-delivery coating 520 or 620 described above) to a substrate, the method including:

1. Preparation of substrates and cleaning (some substrates also require a primer), 2. Positioning of substrates in coating equipment,
3. Immersion of substrate into the coating reagents,
4. Extraction of substrates from coating reagents,
5. Curing by UV radiation, and
6. Sterilization, quality control and packaging.

In some embodiments, the entire process for simultaneously coating a plurality (e.g., 2, 16, 64, 144 or more or other numbers coated simultaneously or substantially simultaneously) of urinary catheters of the present invention will take a manufacturer less than ten (10) minutes to complete.

In other embodiments, the present invention utilizes other coating techniques as alternative or additional methods, including but not limited to: ink jetting, wipe coating and/or spray coating.

In some embodiments, the one or more coatings on the urinary catheter of the present invention include silicone, silver, and/or Ag-PTFE (a silver-enhanced nanocoating that includes silver nanoparticles and/or silver nanolayers sputtered or otherwise deposited on a layer of polytetrafluoroethylene (PTFE) and optionally anneals to form nanometer-sized silver particles (or "islands") on the PTFE surface) to prevent or inhibit formation of a bacterial film on the catheter. In other embodiments, the catheters of the present invention are coated with and/or made of one or both of two main types of antifouling materials: ones made of hydrophilic materials (e.g. SAM-OEG, PEG, POEGMA) [46-48] and ones made of polyzwitterions (e.g., polyMPC, polyCBMA, polySBMA) [49-51]. They repel foulants by forming a barrier of hydration layer on the surface [52, 53]. This hydration layer is formed through hydrogen bonding and/or ionic solvation.

SUMMARY OF SOME EMBODIMENTS OF THE PRESENT INVENTION

In some embodiments, the present invention provides an apparatus that includes a catheter 110 that includes a flexible longitudinal body portion 111 having a proximal end and a distal end, wherein the catheter 110 includes: a first longitudinal (drainage) channel 109 that extends through the body portion 111 from a proximal-end opening to at least one distal-end opening 114 and/or 117 adjacent the distal end of the body portion 111 of the catheter 110; an inflatable balloon portion 112 mounted on the body portion 111 of the catheter configured to be inflated once the inflatable balloon portion 112 is in a bladder 221 of a patient; a first inflation duct 113 extending from the proximal end of the body portion 111 of the catheter and in fluid communication with the inflatable balloon portion 112; and one or more first intermediate side openings 115 and/or 116 in the catheter that are located between the inflatable balloon portion 112 and the proximal end of the body portion 111, wherein the first intermediate side opening 115 and/or 116 extends from the first (drainage) channel 109 through to an external side of the catheter 110.

In some embodiments of the apparatus, the catheter further includes a second longitudinal (fluid injection) channel that extends through the body portion from a proximal-end second channel opening to at least one distal-end second channel opening adjacent the distal end of the body portion of the catheter.

In some embodiments of the apparatus, the catheter further includes a second intermediate side opening in the catheter that is located between the inflatable balloon and the proximal end of the body portion, wherein the second intermediate side opening extends from the first (drainage) channel through to an external side of the catheter.

In some embodiments of the apparatus, the catheter further includes a proximal end stop configured to be at a predetermined distance from the first intermediate side opening.

In some embodiments of the apparatus, the catheter further includes a hydrophilic outer surface coating.

Some embodiments of the apparatus further include a medicament-delivery sheath 120 that includes: a flexible body portion having a proximal end and a distal end, wherein the flexible body portion of the medicament-delivery sheath 120 includes a first longitudinal (medicament injection) duct 152 that extends through the body portion of the medicament-delivery sheath from a proximal-end opening to, and in fluid communication with, a first intermediate side opening between the proximal end and the distal end of the medicament-delivery sheath, wherein the flexible body portion of the medicament-delivery sheath is stiffer than the flexible body portion of the catheter, wherein the medicament-delivery sheath is configured to be removably inserted into the catheter, and wherein the first side opening of the medicament-delivery sheath is located to be adjacent to the first side opening in the catheter when the medicament-delivery sheath is inserted to a first predetermined distance into the catheter.

In some embodiments of the apparatus having the medicament-delivery sheath 120, at least a first longitudinal length of the first longitudinal channel of the catheter has a non-cylindrical keyed cross-sectional internal shape, and at least a first longitudinal length of the medicament-delivery sheath has a non-cylindrical keyed cross-sectional external shape corresponding to the non-cylindrical keyed internal shape of the first longitudinal channel of the catheter, in order that the first side opening of the medicament-delivery sheath is located adjacent to the first side opening in the catheter when the medicament-delivery sheath is inserted to the first predetermined distance into the catheter.

In some embodiments of the apparatus having the medicament-delivery sheath 120, the catheter further includes a second intermediate side opening in the catheter that is located between the inflatable balloon and the proximal end of the body portion, wherein the second intermediate side opening extends from the first (drainage) channel of the catheter through to an external side of the catheter, the medicament-delivery sheath further includes a second intermediate side opening in the medicament-delivery sheath that is located between the proximal end and the distal end of the medicament-delivery sheath and is in fluid communication with the first longitudinal duct, and the second side opening of the medicament-delivery sheath is located to be adjacent to the second side opening in the catheter when the medicament-delivery sheath is inserted to a first predetermined distance into the catheter.

In some embodiments of the apparatus having the medicament-delivery sheath 120, the catheter further includes a second intermediate side opening 155 in the catheter that is located between the inflatable balloon and the proximal end of the body portion, wherein the second intermediate side opening extends to a second (drainage) channel through from an external side of the catheter, the medicament-delivery sheath further includes the second longitudinal (medicament withdrawal) duct that extends through the body portion of the medicament-delivery sheath from a proximal-end opening to, in fluid communication with, a second intermediate side opening between the proximal end and the distal end of the medicament-delivery sheath, and the second side opening of the medicament-delivery sheath is located to be adjacent to the second intermediate side opening in the catheter when the medicament-delivery sheath is inserted to a first predetermined distance into the catheter.

In some embodiments of the apparatus having the medicament-delivery sheath 120, the medicament-delivery sheath further includes a distal tip opening adjacent the distal end of the flexible body portion of the medicament-delivery sheath, and in fluid communication with the first longitudinal (medicament injection) duct.

Some embodiments of the apparatus further include a light-delivery sheath 130 configured to be removably inserted into the catheter, wherein the light-delivery sheath includes: a flexible longitudinal body portion having a proximal end and a distal end, wherein the flexible longitudinal body portion of the light-delivery sheath is stiffer than the flexible longitudinal body portion of the catheter, wherein the light-delivery sheath is configured to be removably inserted into the catheter, wherein the light-delivery sheath includes a light-propagation channel.

In some embodiments of the apparatus having the light-delivery sheath 130, the apparatus further includes a light source configured to be operably coupled to the light-delivery sheath, wherein the light source outputs one or more wavelength bands of light that are effective to kill or inactivate certain microbes.

In some embodiments of the apparatus having the light-delivery sheath 130, the apparatus further includes a light source configured to be operably coupled to the light-delivery sheath, wherein the light source outputs one or more ultraviolet wavelength bands of light each having central wavelengths in a range of 260 nm to 300 nm and that are effective to kill or inactivate certain microbes.

In some embodiments of the apparatus having the light-delivery sheath 130, the apparatus further includes a light source configured to be operably coupled to the light-delivery sheath, wherein the light source outputs one or more wavelength bands of light each having central wavelengths in a range of 360 nm to 420 nm and that are effective to kill or inactivate microbes.

In some embodiments of the apparatus having the light-delivery sheath 130, the apparatus further includes a light source configured to be operably coupled to the light-delivery sheath, wherein the light source outputs a plurality of wavelength bands of light at least one of which having a central wavelength in a range of 260 nm to 300 nm; a light-source controller that is programmable to control the light source to output pulsed light at a plurality of different wavelengths for a plurality of different pulse durations in order to control a dosage of each of the plurality of different wavelengths; and a motorized light-delivery sheath removal unit operably connected to the light-source controller and programmed to withdraw the light-delivery sheath at a rate that combined with the controlled dosage of each of the plurality of different wavelengths is effective to kill or inactivate certain microbes.

Some embodiments of the apparatus further include a light-delivery-and-imaging sheath 140 configured to be removably inserted into the catheter, wherein the light-delivery-and-imaging sheath includes: a flexible longitudinal body portion having a proximal end and a distal end, wherein the flexible longitudinal body portion of the light-delivery-and-imaging sheath is stiffer than the flexible longitudinal body portion of the catheter, wherein the light-delivery-and-imaging sheath is configured to be removably inserted into the catheter, wherein the light-delivery-and-imaging sheath includes a light-propagation channel and a fiber-optic-bundle imaging channel.

In some embodiments of the apparatus having the light-delivery-and-imaging sheath 140, the apparatus further includes an imaging display screen operably connectable to the light-delivery-and-imaging sheath and configured to display an image of tissue in a patient's genitourinary tract, a light source configured to be operably coupled to the light-delivery-and-imaging sheath, wherein the light source outputs one or more wavelength bands of light that are effective to kill or inactivate certain microbes.

In some embodiments of the apparatus having the light-delivery-and-imaging sheath 140, the apparatus further includes a light source configured to be operably coupled to the light-delivery-and-imaging sheath, wherein the light source outputs one or more ultraviolet wavelength bands of light each having central wavelengths in a range of 260 nm to 300 nm and that are effective to kill or inactivate certain microbes.

In some embodiments of the apparatus having the light-delivery-and-imaging sheath 140, the apparatus further includes a light source configured to be operably coupled to the light-delivery sheath, wherein the light source outputs one or more wavelength bands of light each having central wavelengths in a range of 360 nm to 420 nm and that are effective to kill or inactivate microbes.

In some embodiments of the apparatus having the light-delivery-and-imaging sheath 140, the apparatus further includes a light source configured to be operably coupled to the light-delivery sheath, wherein the light source outputs a plurality of wavelength bands of light at least one of which having a central wavelength in a range of 260 nm to 300 nm; a light-source controller that is programmable to control the light source to output pulsed light at a plurality of different wavelengths for a plurality of different pulse durations in order to control a dosage of each of the plurality of different wavelengths; and a motorized light-delivery sheath removal unit operably connected to the light-source controller and programmed to withdraw the light-delivery sheath at a rate that combined with the controlled dosage of each of the plurality of different wavelengths is effective to kill or inactivate certain microbes.

Some embodiments of the invention use a method that includes providing a catheter that includes a flexible longitudinal body portion having a proximal end and a distal end, wherein the catheter includes: a first longitudinal (drainage) channel that extends through the body portion from a proximal-end opening to at least one distal-end opening adjacent the distal end of the body portion of the catheter, an inflatable balloon portion mounted on the body portion of the catheter configured to be inflated once the inflatable balloon portion is in a bladder of a patient, a first inflation duct extending from the proximal end of the body portion of the catheter and in fluid communication with the inflatable balloon portion, and a first intermediate side opening in the catheter that is located between the inflatable balloon and the proximal end of the body portion, wherein the first intermediate side opening extends from the first (drainage) channel through to an external side of the catheter; providing a sheath that includes a flexible longitudinal body portion having a proximal end and a distal end and a central channel, wherein the sheath includes: a first intermediate side opening in the sheath that is located between the distal end and the proximal end of the body portion, wherein the first intermediate side opening in the sheath extends from the central channel through to an external side of the sheath and is located to communicate with the first intermediate side opening in the catheter; and injecting a hemostatic medicament through the central channel and first intermediate side opening in the sheath and the first intermediate side opening in the catheter in order to treat bleeding.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should be, therefore, determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

What is claimed is:

1. An apparatus comprising:
   a catheter that includes a flexible longitudinal body portion having a proximal end and a distal end, wherein the catheter includes:
      a first longitudinal channel that extends through the body portion from a proximal-end opening to at least one distal-end opening adjacent the distal end of the body portion of the catheter;
      an inflatable balloon portion mounted on the body portion of the catheter configured to be inflated once the inflatable balloon portion is in a bladder of a patient;
      a first inflation duct extending from the proximal end of the body portion of the catheter and in fluid communication with the inflatable balloon portion; and
      a first intermediate side opening in the catheter that is located between the inflatable balloon portion and the proximal end of the body portion, wherein the first intermediate side opening extends from the first channel through to an external side of the catheter, and
   a medicament-delivery sheath that includes:
      a flexible body portion having a proximal end and a distal end,
   wherein the flexible body portion of the medicament-delivery sheath includes a first longitudinal duct that extends through the body portion of the medicament-delivery sheath from a proximal-end opening to, and in fluid communication with, a first intermediate side opening between the proximal end and the distal end of the medicament-delivery sheath,
      wherein the flexible body portion of the medicament-delivery sheath is stiffer than the flexible body portion of the catheter,
      wherein the medicament-delivery sheath is configured to be removably inserted into the catheter, and
      wherein the first side opening of the medicament-delivery sheath is located to be adjacent to the first side opening in the catheter when the medicament-delivery sheath is inserted to a first predetermined distance into the catheter.

2. The apparatus of claim 1, wherein the catheter further includes a second longitudinal channel that extends through the body portion from a proximal-end second channel opening to at least one distal-end second channel opening adjacent the distal end of the body portion of the catheter.

3. The apparatus of claim 1, wherein the catheter further includes a second intermediate side opening in the catheter that is located between the inflatable balloon portion and the proximal end of the body portion, wherein the second intermediate side opening extends from the first channel through to an external side of the catheter.

4. The apparatus of claim 1, wherein the catheter further includes a proximal end stop configured to be at a predetermined distance from the first intermediate side opening.

5. The apparatus of claim 1, wherein the catheter further includes a hydrophilic outer surface coating.

6. The apparatus of claim 1,
   wherein at least a first longitudinal length of the first longitudinal channel of the catheter has a non-cylindrical keyed cross-sectional internal shape, and
   wherein at least a first longitudinal length of the medicament-delivery sheath has a non-cylindrical keyed cross-sectional external shape corresponding to the non-cylindrical keyed internal shape of the first longitudinal channel of the catheter, in order that the first side opening of the medicament-delivery sheath is located adjacent to the first side opening in the catheter when the medicament-delivery sheath is inserted to the first predetermined distance into the catheter.

7. The apparatus of claim 1,
   wherein the catheter further includes a second intermediate side opening in the catheter that is located between the inflatable balloon portion and the proximal end of the body portion, wherein the second intermediate side opening extends from the first channel of the catheter through to an external side of the catheter,
   wherein the medicament-delivery sheath further includes a second intermediate side opening in the medicament-delivery sheath that is located between the proximal end and the distal end of the medicament-delivery sheath and is in fluid communication with the first longitudinal duct, and
   wherein the second side opening of the medicament-delivery sheath is located to be adjacent to the second side opening in the catheter when the medicament-delivery sheath is inserted to a first predetermined distance into the catheter.

8. The apparatus of claim 1,
   wherein the catheter further includes a second intermediate side opening in the catheter that is located between the inflatable balloon portion and the proximal end of the body portion, wherein the second intermediate side opening extends from the first channel through to an external side of the catheter,
   wherein the medicament-delivery sheath further includes a second longitudinal duct that extends through the body portion of the medicament-delivery sheath from a proximal-end opening to, in fluid communication with, a second intermediate side opening between the proximal end and the distal end of the medicament-delivery sheath, and
   wherein the second side opening of the medicament-delivery sheath is located to be adjacent to the second intermediate side opening in the catheter when the medicament-delivery sheath is inserted to a first predetermined distance into the catheter.

9. The apparatus of claim 1, wherein the medicament-delivery sheath further includes a distal tip opening adjacent the distal end of the flexible body portion of the medicament-delivery sheath, and in fluid communication with the first longitudinal duct.

10. The apparatus of claim 1, further comprising:

a light-delivery sheath configured to be removably inserted into the catheter, wherein the light-delivery sheath includes:
  a flexible longitudinal body portion having a proximal end and a distal end,
  wherein the flexible longitudinal body portion of the light-delivery sheath is stiffer than the flexible longitudinal body portion of the catheter,
  wherein the light-delivery sheath is configured to be removably inserted into the catheter,
  wherein the light-delivery sheath includes a light-propagation channel.

11. The apparatus of claim 10, further comprising:
a light source configured to be operably coupled to the light-delivery sheath, wherein the light source outputs one or more wavelength bands of light that are effective to kill or inactivate certain microbes.

12. The apparatus of claim 10, further comprising:
a light source configured to be operably coupled to the light-delivery sheath, wherein the light source outputs one or more ultraviolet wavelength bands of light each having central wavelengths in a range of 260 nm to 300 nm and that are effective to kill or inactivate certain microbes.

13. The apparatus of claim 10, further comprising:
a light source configured to be operably coupled to the light-delivery sheath, wherein the light source outputs one or more wavelength bands of light each having central wavelengths in a range of 360 nm to 420 nm and that are effective to kill or inactivate microbes.

14. The apparatus of claim 10, further comprising:
a light source configured to be operably coupled to the light-delivery sheath, wherein the light source outputs a plurality of wavelength bands of light at least one of which having a central wavelength in a range of 260 nm to 300 nm;
a light-source controller that is programmable to control the light source to output pulsed light at a plurality of different wavelengths for a plurality of different pulse durations in order to control a dosage of each of the plurality of different wavelengths; and
a motorized light-delivery sheath removal unit operably connected to the light-source controller and programmed to withdraw the light-delivery sheath at a rate that combined with the controlled dosage of each of the plurality of different wavelengths is effective to kill or inactivate certain microbes.

15. An apparatus comprising:
a catheter that includes a flexible longitudinal body portion having a proximal end and a distal end, wherein the catheter includes:
  a first longitudinal channel that extends through the body portion from a proximal-end opening to at least one distal-end opening adjacent the distal end of the body portion of the catheter;
an inflatable balloon portion mounted on the body portion of the catheter configured to be inflated once the inflatable balloon portion is in a bladder of a patient;
a first inflation duct extending from the proximal end of the body portion of the catheter and in fluid communication with the inflatable balloon portion; and
a first intermediate side opening in the catheter that is located between the inflatable balloon portion and the proximal end of the body portion, wherein the first intermediate side opening extends from the first channel through to an external side of the catheter; and a light-delivery-and-imaging sheath configured to be removably inserted into the catheter including:
  a flexible longitudinal body portion having a proximal end and a distal end,
  wherein the flexible longitudinal body portion of the light-delivery-and-imaging sheath is stiffer than the flexible longitudinal body portion of the catheter,
  wherein the light-delivery-and-imaging sheath is configured to be removably inserted into the catheter,
  wherein the light-delivery-and-imaging sheath includes a light-propagation channel and a fiber-optic-bundle imaging channel.

16. The apparatus of claim 15, wherein the catheter further includes a hydrophilic outer surface coating.

17. The apparatus of claim 16, further comprising an imaging display screen operably connectable to the light-delivery-and-imaging sheath and configured to display an image of tissue in a light source configured to be operably coupled to the light-delivery-and-imaging sheath, wherein the light source outputs one or more wavelength bands of light that are effective to kill or inactivate certain microbes.

18. The apparatus of claim 16, further comprising a light source configured to be operably coupled to a light-delivery sheath configured to be removably inserted into the catheter, wherein the light source outputs one or more ultraviolet wavelength bands of light each having central wavelengths in a range of 260 nm to 300 nm and that are effective to kill or inactivate certain microbes.

19. The apparatus of claim 16, further comprising a light source configured to be operably coupled to a light-delivery sheath configured to be removably inserted into the catheter, wherein the light source outputs one or more wavelength bands of light each having central wavelengths in a range of 360 nm to 420 nm and that are effective to kill or inactivate microbes.

20. The apparatus of claim 16, further comprising:
a light source configured to be operably coupled to a light-delivery sheath configured to be removably inserted into the catheter, wherein the light source outputs a plurality of wavelength bands of light at least one of which having a central wavelength in a range of 260 nm to 300 nm;
a light-source controller that is programmable to control the light source to output pulsed light at a plurality of different wavelengths for a plurality of different pulse durations in order to control a dosage of each of the plurality of different wavelengths; and
a motorized light-delivery sheath removal unit operably connected to the light-source controller and programmed to withdraw the light-delivery sheath at a rate that combined with the controlled dosage of each of the plurality of different wavelengths is effective to kill or inactivate certain microbes.

21. A method comprising:
providing a catheter that includes a flexible longitudinal body portion having a proximal end and a distal end, wherein the catheter includes:
  a first longitudinal channel that extends through the body portion from a proximal-end opening to at least one distal-end opening adjacent the distal end of the body portion of the catheter,
  an inflatable balloon portion mounted on the body portion of the catheter configured to be inflated once the inflatable balloon portion is in a bladder of a patient, a first inflation duct extending from the proximal end of the body portion of the catheter and in fluid communication with the inflatable balloon portion, and a first intermediate side opening in the catheter that is located between the inflatable balloon portion and the proximal end of the body portion, wherein the first intermediate side opening extends from the first channel through to an external side of the catheter;

providing a sheath that includes a flexible longitudinal body portion having a proximal end and a distal end and a central channel, wherein the sheath includes:

a first intermediate side opening in the sheath that is located between the distal end and the proximal end of the body portion, wherein the first intermediate side opening in the sheath extends from the central channel through to an external side of the sheath and is located to communicate with the first intermediate side opening in the catheter; and injecting a hemostatic medicament through the central channel and first intermediate side opening in the sheath and the first intermediate side opening in the catheter in order to treat bleeding.

\* \* \* \* \*